United States Patent
Lamberth et al.

(10) Patent No.: US 8,003,626 B2
(45) Date of Patent: Aug. 23, 2011

(54) PYRAZOLE-4-CARBOXAMIDE DERIVATIVES AS MICROBIOCIDES

(75) Inventors: Clemens Lamberth, Basel (CH); Camilla Corsi, Basel (CH); Josef Ehrenfreund, Basel (CH); Hans Tobler, Basel (CH); Harald Walter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 541 days.

(21) Appl. No.: 11/996,094

(22) PCT Filed: Jul. 17, 2006

(86) PCT No.: PCT/EP2006/007001
§ 371 (c)(1), (2), (4) Date: Jan. 18, 2008

(87) PCT Pub. No.: WO2007/009717
PCT Pub. Date: Jan. 25, 2007

(65) Prior Publication Data
US 2008/0188442 A1   Aug. 7, 2008

(30) Foreign Application Priority Data
Jul. 18, 2005   (EP) .................................. 05015526

(51) Int. Cl.
*A01N 57/00* (2006.01)
*C07D 231/06* (2006.01)

(52) U.S. Cl. ........................................ 514/94; 548/379.1
(58) Field of Classification Search ................... None
See application file for complete search history.

(56) References Cited

FOREIGN PATENT DOCUMENTS

| EP | 0824099 A1 | 2/1998 |
|---|---|---|
| WO | 9311117 | 6/1993 |
| WO | 2004035545 | 4/2004 |
| WO | 2004035589 | 4/2004 |
| WO | 2004058723 | 7/2004 |
| WO | 2004106324 | 12/2004 |
| WO | 2005028485 A1 | 3/2005 |
| WO | 2005040152 | 5/2005 |

OTHER PUBLICATIONS

Chan et al., caplus an 2005:395299.*

\* cited by examiner

*Primary Examiner* — Sun Jae Loewe
(74) *Attorney, Agent, or Firm* — James Cueva

(57) ABSTRACT

Compounds of the formula I in which the substituents are as defined in claim 1 are suitable for use as microbiocides.

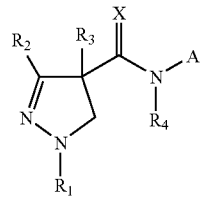

(I)

10 Claims, No Drawings

PYRAZOLE-4-CARBOXAMIDE DERIVATIVES AS MICROBIOCIDES

This application is a National Stage Entry under 35 USC §371 of International application serial number PCT/EP2006/007001, filed on Jul. 17, 2006, which claims priority to EP 05015526.6, filed on Jul. 18, 2005, the contents of which are incorporated herein by reference.

The present invention relates to novel microbiocidally active, in particular fungicidally active, carboxamides/thioamides. It further relates to compositions which comprise these compounds and to their use in agriculture or horticulture for controlling or preventing infestation of plants by phytopathogenic microorganisms, preferably fungi.

Pyrazole carboxamides/thioamides having microbiocidal activity are described, for example in EP-0-824-099 and WO 93/11117.

It has been found that novel dihydropyrazole carboxamides/thioamides have microbiocidal activity.

The present invention thus provides compounds of the formula I

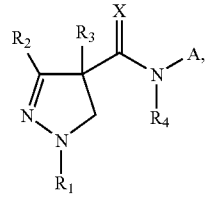

(I)

wherein $R_1$ is $C_{1-4}$ alkyl, $C_{1-4}$ haloalkyl, $C_{1-4}$ alkoxy($C_{1-4}$)alkyl or $C_{1-4}$ haloalkoxy($C_{1-4}$)alkyl;

$R_2$ is $C_{1-4}$ haloalkyl, $C_{1-4}$ alkyl, $C_{1-4}$ alkoxy($C_{1-4}$)alkyl, $C_{1-4}$ haloalkoxy or $C_{1-4}$ haloalkoxy($C_{1-4}$)alkyl;

$R_3$ is hydrogen, $C_{1-4}$ alkyl, $C_{2-4}$ alkenyl, $C_{2-4}$ alkynyl, halogen or cyano;

$R_4$ is hydrogen, $C_{1-4}$ alkyl, $CH_2CH=CHR_{4a}$, $CH_2C\equiv CR_{4b}$ or $COR_{4c}$;

$R_{4a}$ and $R_{4b}$ are each, independently, hydrogen, $C_1$-$C_6$alkyl, $C_1$-$C_6$haloalkyl, $C_2$-$C_6$alkenyl, $C_2$-$C_6$alkynyl, $C_3$-$C_7$cycloalkyl, $COOC_1$-$C_4$alkyl, $COOC_3$-$C_6$alkenyl, $COOC_3$-$C_6$alkynyl or CN;

$R_{4c}$ is $C_1$-$C_6$alkyl, $C_1$-$C_6$alkyl substituted by halogen, $C_1$-$C_6$alkoxy or $C_1$-$C_6$haloalkoxy; or is $C_1$-$C_6$alkylthio, $C_1$-$C_6$haloalkylthio, $C_1$-$C_6$alkoxy, $C_1$-$C_6$haloalkoxy; $C_3$-$C_6$alkenyloxy or $C_3$-$C_6$haloalkenyloxy; $C_3$-$C_6$alkynyloxy or $C_3$-$C_6$haloalkynyloxy;

X is oxygen or sulfur; and

A is a group

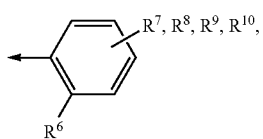

(A1)

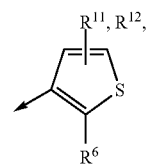

(A2)

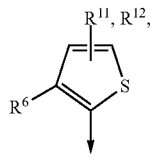

(A3)

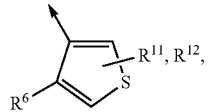

(A4)

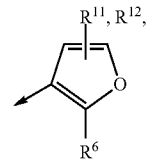

(A5)

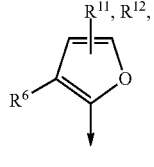

(A6)

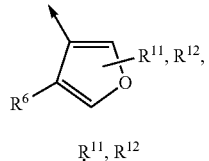

(A7)

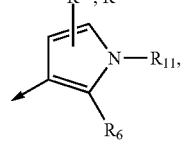

(A8)

(A9)

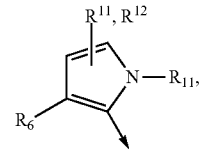

(A10)

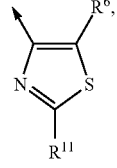

(A11)

-continued
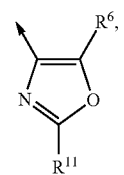 (A12)
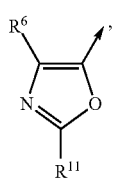 (A13)
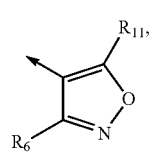 (A14)
 (A15)
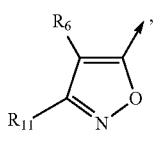 (A16)
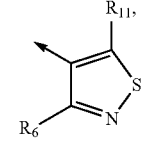 (A17)
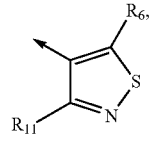 (A18)
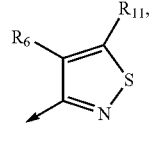 (A19)
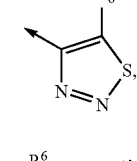 (A20)
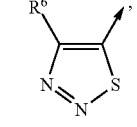 (A21)
-continued
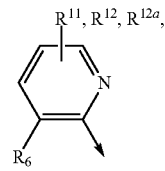 (A22)
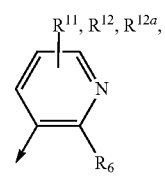 (A23)
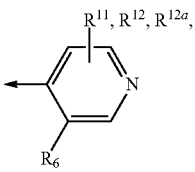 (A24)
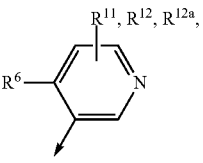 (A25)
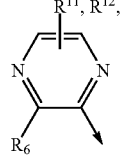 (A26)
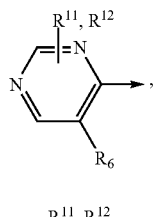 (A27)
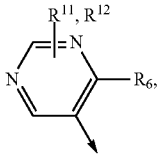 (A28)
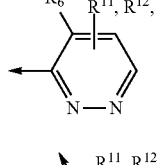 (A29)
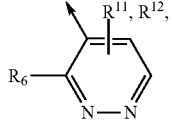 (A30)

-continued

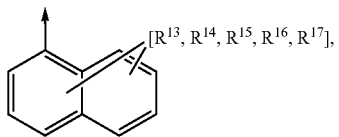
(A31)

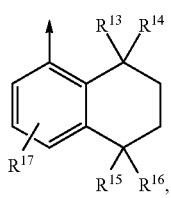
(A32)

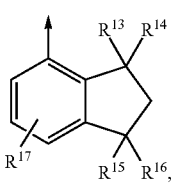
(A33)

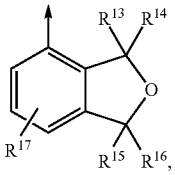
(A34)

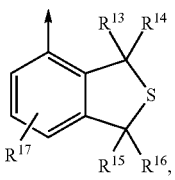
(A35)

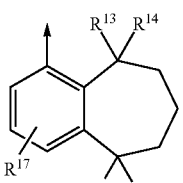
(A36)

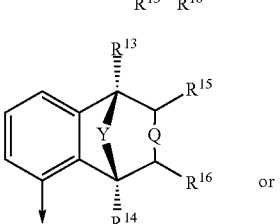
(A37)

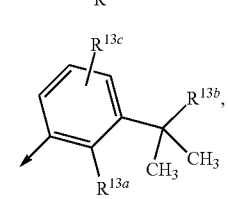
or (A38)

wherein
$R^6$ is a $C_{1-12}$ alkyl, $C_{2-12}$ alkenyl or $C_{2-12}$ alkynyl group, which may be substituted by 1 to 6 substituents, each substituent independently selected from halogen, cyano, $C_{1-4}$ alkoxy, $C_{1-4}$ thioalkyl, COO—$C_{1-4}$ alkyl, =N—OH, =N—O—($C_{1-4}$ alkyl), $C_{3-8}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and $C_{4-8}$ cycloalkenyl, which may itself be substituted by 1 to 3 substituents, each independently selected from $C_{1-4}$ alkyl, halogen, $C_{1-4}$ alkoxy and $C_{1-4}$ haloalkoxy;

or $R^6$ is a $C_{3-8}$ cycloalkyl, $C_{4-8}$ cycloalkenyl or $C_{5-8}$ cycloalkadienyl group, which may be substituted by 1 to 3 substituents, each independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and phenyl, which may itself be substituted by 1 to 5 independently selected halogen atoms;

or $R^6$ is a $C_{6-12}$ bicycloalkyl, $C_{6-12}$ bicycloalkenyl or $C_{6-12}$ bicycloalkadienyl group, which may be substituted by 1 to 3 substituents, each independently selected from halogen, $C_{1-4}$ alkyl and $C_{1-4}$ haloalkyl;

or $R^6$ is phenyl, which may be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ alkylthio, $C_{1-4}$ alkylthio, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl), $(Z)_pC\!\!=\!\!CR^{25}$, $(Z)_pCR^{28}\!\!=\!\!CR^{26}R^{27}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl);

or $R^6$ is a 5-6 membered heterocyclic ring, wherein the heterocyclic ring contains 1 to 3 heteroatoms, each heteroatom independently chosen from oxygen, sulphur and nitrogen, wherein the heterocyclic ring may be substituted 1 to 3 substituents, each independently selected from halogen, cyano, nitro, $C_{1-4}$ alkyl, $C_{1-4}$ haloalkyl, $C_{1-4}$ alkoxy, $C_{1-4}$ alkylthio, $C_{1-4}$ alkylthio, $C_{1-4}$ haloalkoxy, C(H)=N—O—($C_{1-6}$ alkyl) and C($C_{1-16}$ alkyl)=N—O—($C_{1-6}$ alkyl), $C_{2-5}$ alkenyl, $C_{2-5}$ alkynyl, CHO, COO$C_1$-$C_6$alkyl, $C_1$-$C_4$alkoxy-$C_1$-$C_4$alkyl, $C_1$-$C_4$haloalkoxy-$C_1$-$C_4$alkyl, $(Z)_pC\!\!=\!\!CR^{25}$, $(Z)_pCR^{28}\!\!=\!\!CR^{26}R^{27}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and wherein two substituents on adjacent carbon atoms of the 5-6 membered heterocyclic ring together may form a group —$CR^{6a}$—$CR^{6a}$=$CR^{6a}CR^{6a}$, wherein each $R^{6a}$ independently is selected from hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl);

or $R^6$ is an aliphatic saturated or unsaturated group containing 3 to 13 carbon atoms and at least one silicon atom, wherein the aliphatic group may contain 1 to 3 heteroatoms, each heteroatom independently selected from oxygen, nitrogen and sulphur, and wherein the aliphatic group may be substituted by 1 to 4 independently selected halogen atoms;

or $R^6$ is $(CR^aR^b)_m$-Cy-$(CR^cR^d)_n$—$Y_1$;

or $R^6$ is $C_{1-6}$alkoxy, $C_{1-6}$haloalkoxy, $C_{2-6}$alkenyloxy, $C_{2-6}$haloalkenyloxy, $C_{2-6}$alkinyloxy, $C_{3-6}$cycloalkyloxy, $C_{1-4}$alkyl-$C_{3-7}$cycloalkyloxy, $C_{5-7}$cycloalkenyloxy or $C_{1-4}$alkyl-$C_{5-7}$cycloalkenyloxy;

Z is $C_{1-4}$ alkylene;

p is 0 or 1;

$R^{25}$ is hydrogen, halogen, $C_{1-4}$alkyl, $C_{1-4}$haloalkyl, $C_{1-4}$alkoxy$(C_{1-4})$alkyl, $C_{1-4}$haloalkoxy$(C_{1-4})$alkyl or $Si(C_{1-4}$ alkyl$)_3$;

$R^{26}$ and $R^{27}$ are each, independently, hydrogen, halogen, $C_{1-4}$ alkyl or $C_{1-4}$ haloalkyl;

$R^{28}$ is hydrogen, $C_{1-4}$ alkyl or $C_{1-4}$ haloalkyl;

$R^a$, $R^b$, $R^c$ and $R^d$ are each, independently, hydrogen or a $C_{1-4}$ alkyl group, which may substituted by 1 to 6 substituents, each substituent independently selected from halogen, hydroxy, cyano, carboxyl, methoxycarbonyl, ethoxycarbonyl, methoxy, ethoxy, methylsulfonyl, ethylsulfonyl, difluoromethoxy, trifluoromethoxy, trifluoromethylthio and trifluorothiomethoxy;

Cy is a carbocyclic or heterocyclic 3-7 membered ring, which may be saturated, unsaturated or aromatic and which may contain a silicon atom as a ring member, wherein $(CR^aR^b)_m$ and $(CR^cR^d)_n$ may be bound either to the same carbon or silicon atom of Cy or to different atoms separated by 1, 2 or 3 ring members, wherein the carbocyclic or heterocyclic 3-7 membered ring may substituted by 1 to 6 substituents, each substituent independently selected from halogen, $C_{1-4}$ alkyl, $C_{2-4}$ alkenyl, $C_{1-4}$ haloalkyl, $C_{1-4}$ alkoxy and halo-$C_{1-4}$ alkoxy;

$Y_1$ is $Si(O_{p1}Z^1)(O_qZ^2)(O_sZ^3)$ and provided that Cy contains a silicon atom as a ring member then $Y_1$ may also be hydrogen;

$Z^1$ and $Z^2$ are independently methyl or ethyl;

$Z^3$ is a $C_{1-4}$ alkyl or a $C_{2-4}$ alkenyl group, which may be interrupted by one heteroatom selected from O, S and N, and wherein the $C_{1-4}$ alkyl or $C_{2-4}$ alkenyl group may be substituted by 1 to 3 independently selected halogen atoms;

m and n are each independently 0, 1, 2 or 3;

$p_1$, q and s are each independently 0 or 1;

$R^7$, $R^8$, $R^9$, $R^{10}$, $R^{11}$, $R^{12}$ and $R^{12a}$ are each, independently, hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ thioalkyl or $C_{1-4}$ thiohaloalkyl;

$R^{13}$, $R^{14}$, $R^{15}$, $R^{16}$ and $R^{17}$ are each, independently, hydrogen, halogen, cyano, nitro, $C_{1-4}$ alkyl, $C(O)CH_3$, $C_{1-4}$ haloalkyl, $C_{1-4}$ alkoxy, $C_{1-4}$ haloalkoxy, $C_{1-4}$ thioalkyl, $C_{1-4}$ thiohaloalkyl, hydroxymethyl or $C_{1-4}$ alkoxymethyl;

Q is a single or a double bond; and

Y is O, N($R^{18}$), S or $(CR^{19}R^{20})(CR^{21}R^{22})_{m1}(CR^{23}R^{24})_{n1}$;

$R^{18}$ is hydrogen, $C_{1-4}$ alkyl, formyl, $C_{1-4}$ alkoxy$(C_{1-4})$alkyl, $C(=O)C_{1-4}$alkyl, which may be substituted by halogen or $C_{1-4}$-alkoxy, or $C(=O)O$—$C_{1-6}$alkyl, which may be substituted by halogen, $C_{1-4}$ alkoxy or CN;

$R^{19}$, $R^{20}$, $R^{21}$, $R^{22}$, $R^{23}$ and $R^{24}$ are each independently hydrogen, halogen, hydroxy, $C_{1-4}$ alkoxy, $C_{1-6}$ alkyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), $C_{1-6}$ alkenyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), or a 3-7 membered carbocyclic ring, which may contain 1 heteroatom selected from nitrogen and oxygen, and wherein the 3-7 membered carbocyclic ring may be substituted by 1 to 3 methyl groups;

or $R^{19}R^{20}$ together with the carbon atom to which they are attached form a carbonyl-group, a 3-5 membered carbocyclic ring, which may be substituted by 1 to 3 methyl groups, $C_{1-6}$ alkylidene, which may be substituted by 1 to 3 methyl groups, or $C_{3-6}$cycloalkylidene, which may be substituted by 1 to 3 methyl groups;

$m_1$ is 0 or 1;

$n_1$ is 0 or 1;

$R^{13a}$ is a $C_1$-$C_4$alkyl, $C_2$-$C_4$alkenyl or $C_2$-$C_4$alkynyl group, which may be substituted by 1 to 6 substituents, each substituent independently selected from halogen, hydroxy, cyano, $C_1$-$C_4$alkoxycarbonyl, formyl, nitro, $C_1$-$C_4$alkoxy, $C_1$-$C_4$haloalkoxy, $C_1$-$C_4$alkylthio, $C_1$-$C_4$haloalkylthio, HC(OR$^{29}$)=N— and $R^{30}R^{31}$NN=C(H)—;

$R^{29}$, $R^{30}$ and $R^{31}$ independently of one another are hydrogen or $C_1$-$C_4$alkyl;

$R^{13b}$ is a $C_1$-$C_6$alkyl group, which may be substituted by 1 to 6 substituents, each substituent independently selected from halogen, hydroxy, cyano, $C_1$-$C_4$alkoxycarbonyl, formyl, nitro, $C_1$-$C_4$alkoxy, $C_1$-$C_4$haloalkoxy, $C_1$-$C_4$alkylthio, $C_1$-$C_4$haloalkylthio, HC(OR$^{32}$)=N— and $R^{33}R^{34}$NN=C(H)—;

$R^{32}$, $R^{33}$ and $R^{34}$ independently of one another are hydrogen or $C_1$-$C_4$alkyl;

$R^{13c}$ is hydrogen or halogen;

and tautomers/isomers/enantiomers of these compounds.

In compounds of formula I, the arrow depicted in the groups (A1) to (A38) represents a bond to the nitrogen atom of the carboxamide/thioamide group of compounds of formula I.

The alkyl groups occurring in the definitions of the substituents can be straight-chain or branched and are, for example, methyl, ethyl, n-propyl, n-butyl, n-pentyl, n-hexyl, isopropyl, n-butyl, secbutyl, isobutyl or tert-butyl. Alkoxy, alkenyl and alkynyl radicals are derived from the alkyl radicals mentioned. The alkenyl and alkynyl groups can be mono- or di-unsaturated.

Halogen is generally fluorine, chlorine, bromine or iodine, preferably fluorine, bromine or chlorine. This also applies, correspondingly, to halogen in combination with other meanings, such as haloalkyl or haloalkoxy.

Haloalkyl groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloro-methyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoro-propynyl and 4,4,4-trifluorobut-2-yn-1-yl.

Alkoxy is, for example, methoxy, ethoxy, propoxy, i-propoxy, n-butoxy, isobutoxy, sec-butoxy and tert-butoxy; preferably methoxy and ethoxy. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio is, for example, methylthio, ethylthio, propylthio, isopropylthio, n-butylthio, isobutylthio, sec-butylthio or tert-butylthio, preferably methylthio and ethylthio.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

In the context of the present invention $C_{1-12}$ alkyl, $C_{2-12}$ alkenyl or $C_{2-12}$ alkynyl groups, which are substituted by 1 to 6 substituents, for example in the definition of substituent $R^6$, are typically monosubstituted to five-times substituted, more preferably mono-, double- or triple-substituted.

The compounds of formula I, such as compounds of formula I, wherein X is oxygen and $R_4$ is hydrogen, may occur in different tautomeric forms, such as $I_I$ and $I_{II}$:

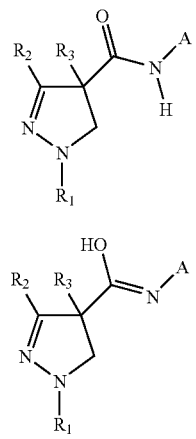

The invention covers all those tautomeric forms.

Some of the compounds of formula I occur as enantiomers. In the case of such enantiomeric compounds of formula I, racemic mixtures of such enantiomers are preferred.

In a preferred group of compounds of formula I, $R_2$ is $C_{1-4}$ haloalkyl, $C_{1-4}$ alkyl, $C_{1-4}$ alkoxy$(C_{1-4})$alkyl or $C_{1-4}$ haloalkoxy$(C_{1-4})$alkyl; and $R_6$ is a $C_{1-12}$ alkyl, $C_{2-12}$ alkenyl or $C_{2-12}$ alkynyl group, which may be substituted by 1 to 6 substituents, each substituent independently selected from halogen, cyano, $C_{1-4}$ alkoxy, $C_{1-4}$ thioalkyl, COO—$C_{1-4}$ alkyl, =N—OH, =N—O—$(C_{1-4}$ alkyl), $C_{3-8}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and $C_{4-8}$ cycloalkenyl, which may itself be substituted by 1 to 3 substituents, each independently selected from $C_{1-4}$ alkyl, halogen, $C_{1-4}$ alkoxy and $C_{1-4}$ haloalkoxy;

or $R^6$ is a $C_{3-8}$ cycloalkyl, $C_{4-8}$ cycloalkenyl or $C_{5-8}$ cycloalkadienyl group, which may be substituted by 1 to 3 substituents, each independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and phenyl, which may itself be substituted by 1 to 5 independently selected halogen atoms;

or $R^6$ is a $C_{6-12}$ bicycloalkyl, $C_{6-12}$ bicycloalkenyl or $C_{6-12}$ bicycloalkadienyl group, which may be substituted by 1 to 3 substituents, each independently selected from halogen, $C_{1-4}$ alkyl and $C_{1-4}$ haloalkyl;

or $R^6$ is phenyl, which may be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl), $(Z)_pC$=$CR^{25}$, $(Z)_pCR^{28}$=$CR^{26}R^{27}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl);

or $R^6$ is a 5-6 membered heterocyclic ring, wherein the heterocyclic ring contains 1 to 3 heteroatoms, each heteroatom independently chosen from oxygen, sulphur and nitrogen, wherein the heterocyclic ring may be substituted 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, C(H)=N—O—($C_{1-6}$ alkyl) and C($C_{1-6}$ alkyl)=N—O—($C_{1-6}$ alkyl), $C_{2-5}$ alkenyl, $C_{2-5}$ alkynyl, CHO, COO$C_{1-6}$alkyl, $C_1$-$C_4$alkoxy-$C_1$-$C_4$alkyl, $C_1$-$C_4$haloalkoxy-$C_1$-$C_4$alkyl, $(Z)_pC$=$CR^{25}$, $(Z)_pCR^{28}$=$CR^{26}R^{27}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl);

or $R^6$ is an aliphatic saturated or unsaturated group containing 3 to 13 carbon atoms and at least one silicon atom, wherein the aliphatic group may contain 1 to 3 heteroatoms, each heteroatom independently selected from oxygen, nitrogen and sulphur, and wherein the aliphatic group may be substituted by 1 to 4 independently selected halogen atoms;

or $R^6$ is $(CR^aR^b)_m$-Cy-$(CR^cR^d)_n$—$Y_1$;

or $R^6$ is $C_{1-6}$alkoxy, $C_{1-6}$haloalkoxy, $C_{2-6}$alkenyloxy, $C_{2-6}$haloalkenyloxy, $C_{2-6}$alkinyloxy, $C_{3-6}$cycloalkyloxy, $C_{1-4}$alkyl-$C_{3-7}$cycloalkyloxy, $C_{5-7}$cycloalkenyloxy or $C_{1-4}$alkyl-$C_{5-7}$cycloalkenyloxy.

In one embodiment of the invention in compounds of formula I X is oxygen.

In another embodiment of the invention in compounds of formula I X is sulfur.

In a preferred group of compounds of formula I
$R_1$ is $C_{1-4}$ alkyl or $C_{1-4}$ alkoxy($C_{1-4}$)alkyl;
$R_2$ is $C_{1-4}$ haloalkyl;
$R_3$ is hydrogen, $C_{1-4}$ alkyl, $C_{2-4}$ alkenyl, $C_{2-4}$ alkynyl, halogen or cyano; and/or
$R_4$ is hydrogen, $C_{1-4}$ alkyl, $CH_2CH=CH_2$ or $CH_2C\equiv CH$.

In a further preferred group of compounds
$R_1$ is $C_{1-4}$ alkyl or $C_{1-4}$ alkoxy($C_{1-4}$)alkyl;
$R_2$ is $C_{1-4}$ haloalkyl;
$R_3$ is hydrogen, $C_{1-4}$ alkyl, $C_{2-4}$ alkenyl, $C_{2-4}$ alkynyl, halogen or cyano; and/or
$R_4$ is hydrogen.

In a further preferred group of compounds
$R_1$ is $C_{1-4}$ alkyl or $C_{1-4}$ alkoxy($C_{1-4}$)alkyl;
$R_2$ is $C_{1-4}$ haloalkyl;
$R_3$ is hydrogen, $C_{1-4}$ alkyl, halogen or cyano; and/or
$R_4$ is hydrogen.

In a further preferred group of compounds
$R_1$ is $C_{1-4}$ alkyl or $C_{1-4}$ alkoxy($C_{1-4}$)alkyl;
$R_2$ is $C_{1-4}$ haloalkyl;
$R_3$ is hydrogen and/or
$R_4$ is hydrogen.

In a further preferred group of compounds
$R_1$ is $C_{1-4}$ alkyl or $C_{1-4}$ alkoxy($C_{1-4}$)alkyl;
$R_2$ is $CHF_2$ or $CF_3$;
$R_3$ is hydrogen and/or
$R_4$ is hydrogen.

In one embodiment of the invention A is A1, A2, A3, A4, A37 or A38.

In another embodiment of the invention A is A1, A2, A3, A4 or A38.

In yet another embodiment of the invention A is A1 or A38.

In yet another embodiment of the invention A is A1, A2, A3 or A4.

In yet another embodiment of the invention A is A1.

In yet another embodiment of the invention A is A38.

In yet another embodiment of the invention A is A37.

In yet another embodiment of the invention A is A2, A3, A4, A5, A6, A7, A8 or A9.

In yet another embodiment of the invention A is A2, A3 or A4.

In yet another embodiment of the invention A is A5, A6 or A7.

In yet another embodiment of the invention A is A8 or A9.

In yet another embodiment of the invention A is A10, A11, A12 or A13.

In yet another embodiment of the invention A is A10 or A1.

In yet another embodiment of the invention A is A12 or A13.

In yet another embodiment of the invention A is A14, A15, A16, A17, A18 or A19.

In yet another embodiment of the invention A is A14, A15 or A16.

In yet another embodiment of the invention A is A17, A18 or A19.

In yet another embodiment of the invention A is A20 or A21.

In yet another embodiment of the invention A is A22, A23, A24 or A25.

In yet another embodiment of the invention A is A26, A27, A28, A29 or A30.

In yet another embodiment of the invention A is A26.

In yet another embodiment of the invention A is A27 or A28.

In yet another embodiment of the invention A is A29 or A30.

In yet another embodiment of the invention A is A31.

In yet another embodiment of the invention A is A32, A33, A34, A35 or A36.

In yet another embodiment of the invention A is A32.

In yet another embodiment of the invention A is A33, A34 or A35.

In yet another embodiment of the invention A is A36.

Preference is given to those compounds of the formula I, in which $R^6$ is a $C_{1-12}$ alkyl, $C_{2-12}$ alkenyl or $C_{2-12}$ alkynyl group, which may be substituted by 1 to 6 substituents, each substituent independently selected from halogen, cyano, $C_{1-4}$ alkoxy, $C_{1-4}$ thioalkyl, $COO$—$C_{1-4}$ alkyl, =N—OH, =N—O—($C_{1-4}$ alkyl), $C_{3-8}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and $C_{4-8}$ cycloalkenyl, which may itself be substituted by 1 to 3 substituents, each independently selected from $C_{1-4}$ alkyl, halogen, $C_{1-4}$ alkoxy and $C_{1-4}$ haloalkoxy.

Preference is furthermore given to those compounds of the formula I, in which $R^6$ is a $C_{3-8}$ cycloalkyl, $C_{4-8}$ cycloalkenyl or $C_{5-8}$ cycloalkadienyl group, which may be substituted by 1 to 3 substituents, each independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and phenyl, which may itself be substituted by 1 to 5 independently selected halogen atoms.

Preference is furthermore given to those compounds of the formula I, in which $R^6$ is a $C_{6-12}$ bicycloalkyl, $C_{6-12}$ bicycloalkenyl or $C_{6-12}$ bicycloalkadienyl group, which may be substituted by 1 to 3 substituents, each independently selected from halogen, $C_{1-4}$ alkyl and $C_{1-4}$ haloalkyl.

Preference is furthermore given to those compounds of the formula I, in which $R^6$ is phenyl, which may be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ haloalkylthio, $C(H)=N$—OH, $C(H)=N$—$O(C_{1-6}$ alkyl), $C(C_{1-6}$ alkyl)$=N$—OH, $C(C_{1-6}$ alkyl)$=N$—O—($C_{1-6}$ alkyl), $(Z)_pC\equiv CR^{25}$, $(Z)_pCR^{28}=CR^{26}R^{27}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, $C(H)=N$—OH, $C(H)=N$—$O(C_{1-6}$ alkyl), $C(C_{1-6}$ alkyl)$=N$—OH and $C(C_{1-6}$ alkyl)$=N$—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, $C(H)=N$—OH, $C(H)=N$—$O(C_{1-6}$ alkyl), $C(C_{1-6}$ alkyl)$=N$—OH and $C(C_{1-6}$ alkyl)$=N$—O—($C_{1-6}$ alkyl).

Preference is furthermore given to those compounds of the formula I, in which $R^6$ is a 5-6 membered heterocyclic ring, wherein the heterocyclic ring contains 1 to 3 heteroatoms, each heteroatom independently chosen from oxygen, sulphur and nitrogen, wherein the heterocyclic ring may be substituted 1 to 3 substituents, each independently selected from halogen, cyano, nitro, $C_{1-4}$ alkyl, $C_{1-4}$ haloalkyl, $C_{1-4}$ alkoxy, $C_{1-4}$ alkylthio, $C_{1-4}$ alkylthio, $C_{1-4}$ haloalkoxy, $C(H)=N$—$O$—($C_{1-6}$ alkyl) and $C(C_{1-6}$ alkyl)$=N$—O—($C_{1-6}$ alkyl), $C_{2-5}$ alkenyl, $C_{2-5}$ alkynyl, CHO, $COOC_1$-$C_6$alkyl, $C_1$-$C_4$alkoxy-$C_1$-$C_4$alkyl, $C_1$-$C_4$haloalkoxy-$C_1$-$C_4$alkyl, $(Z)_pC\equiv CR^{25}$, $(Z)_pCR^{28}=CR^{26}R^{27}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, $C(H)=N$—OH, $C(H)=N$—$O(C_{1-6}$ alkyl), $C(C_{1-6}$ alkyl)$=$ $N$—OH and $C(C_{1-6}$ alkyl)$=N$—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and wherein two substituents on adjacent carbon atoms of the 5-6 membered heterocyclic ring together may form a group —$CR^{6a}$=$CR^{6a}$—$CR^{6a}$=$CR^{6a}$—, wherein each $R^{6a}$ independently is selected from hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl).

Preference is furthermore given to those compounds of the formula I, in which $R^6$ is an aliphatic saturated or unsaturated group containing 3 to 13 carbon atoms and at least one silicon atom, wherein the aliphatic group may contain 1 to 3 heteroatoms, each heteroatom independently selected from oxygen, nitrogen and sulphur, and wherein the aliphatic group may be substituted by 1 to 4 independently selected halogen atoms.

Preference is furthermore given to those compounds of the formula I, in which $R^6$ is $(CR^aR^b)_m$-Cy-$(CR^cR^d)_n$—$Y_1$.

$R^7$, $R^8$, $R^9$, $R^{10}$, $R^{11}$, $R^{12}$ and $R^{12a}$ are preferably each, independently, hydrogen or halogen; more preferably hydrogen.

$R^{13}$, $R^{14}$, $R^{15}$, $R^{16}$ and $R^{17}$ are preferably each, independently, hydrogen, halogen or $C_{1-4}$ alkyl, more preferably each, independently, hydrogen or $C_{1-4}$ alkyl.

Preference is furthermore given to those compounds of the formula I, in which $R^6$ is a group of the form

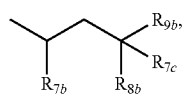

wherein $R_{7b}$ and $R_{7c}$ are independently of each other hydrogen, $C_1$-$C_3$alkyl or $C_1$-$C_3$haloalkyl, and $R_{8b}$ and $R_{9b}$ are independently of each other $C_1$-$C_3$alkyl or $C_1$-$C_3$haloalkyl; or a group of the form

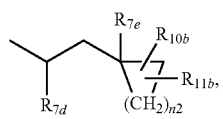

wherein $R_{7d}$ and $R_{7e}$ are independently of each other hydrogen, $C_1$-$C_3$alkyl or $C_1$-$C_3$haloalkyl, and $R_{10b}$ and $R_{11b}$ are independently of each other hydrogen or halogen, and $n_2$ is 1 or 2.

Preference is furthermore given to those compounds of the formula I, in which $R^6$ is $(CR^aR^b)_m$-Cy-$(CR^cR^d)_n$—$Y_1$, wherein Cy is selected from the following rings:

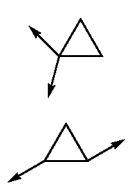

Cy1

Cy2

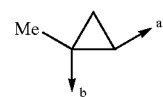 Cy3

 Cy4

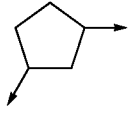 Cy5

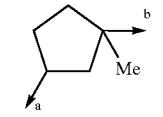 Cy6

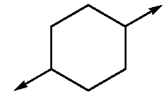 Cy7

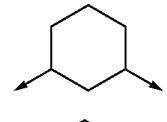 Cy8

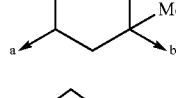 Cy9

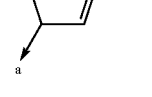 Cy10

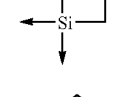 Cy11

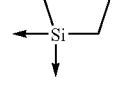 Cy12

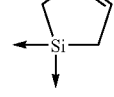 Cy13

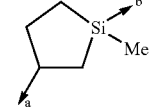 Cy14

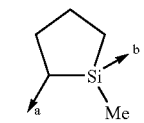 Cy15

| | |
|---|---|
| Cy16 | 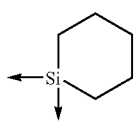 |
| Cy17 | 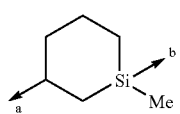 |
| Cy18 | 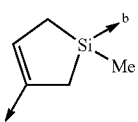 |
| Cy19 | 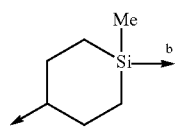 |
| Cy20 | 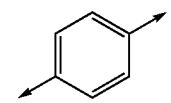 |
| Cy21 | 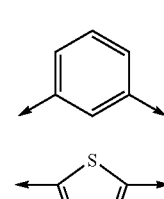 |
| Cy22 | 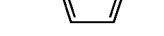 |
| Cy23 | 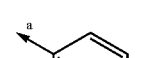 |
| Cy24 | 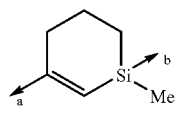 |

The symmetrical nature of Cy1, Cy2, Cy4, Cy5, Cy7, Cy8, Cy11, Cy12, Cy13, Cy16, Cy20, Cy21 and Cy22 means that it does not matter which arrow represents a bond to the moiety $(CR^aR^b)_m$ and which arrow represents a bond to the moiety $(CR^cR^d)_n$. However Cy3, Cy6, Cy9, Cy10, Cy14, Cy15, Cy17, Cy18, Cy19, Cy23 and Cy24 are not symmetric and therefore it does matter which arrow represents a bond to the moiety $(CR^aR^b)_m$ and which arrow represents a bond to the moiety $(CR^cR^d)_n$: for these values of Cy, it is preferred that the arrow labelled "a" represents a bond to the moiety $(CR^aR^b)_m$ [and therefore that the arrow labelled "b" represents a bond to the moiety $(CR^cR^d)_n$]. In this specification Cy3a is the group Cy3 in which the arrow "a" represents a bond to the moiety $(CR^aR^b)_m$; whilst Cy3b is the group Cy3 in which the arrow "b" represents a bond to the moiety $(CR^aR^b)_m$. The same applies mutatis mutandis to Cy6, Cy9, Cy10, Cy14, Cy15, Cy17, Cy18, Cy19, Cy23 and Cy24. In all instances, the "a" group is preferred to the corresponding "b" group.

Preference is furthermore given to those compounds of the formula I, wherein A is A37 and
Q is a single bond; and
Y is $(CR^{19}R^{20})$;
$R^{19}$ and $R^{20}$ are each independently hydrogen, halogen, hydroxy, $C_{1-4}$ alkoxy, $C_{1-6}$ alkyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), $C_{1-6}$ alkenyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), or a 3-7 membered carbocyclic ring, which may contain 1 heteroatom selected from nitrogen and oxygen, and wherein the 3-7 membered carbocyclic ring may be substituted by 1 to 3 methyl groups;
or $R^{19}R^{20}$ together with the carbon atom to which they are attached form a carbonyl-group, a 3-5 membered carbocyclic ring, which may be substituted by 1 to 3 methyl groups, $C_{1-6}$ alkylidene, which may be substituted by 1 to 3 methyl groups, or $C_{3-6}$cycloalkylidene, which may be substituted by 1 to 3 methyl groups.

Within said embodiment preference is furthermore given to those compounds, wherein $R^{19}$ and $R^{20}$ are each independently hydrogen, $C_{1-4}$alkyl or $C_{1-4}$haloalkyl, and $R^{13}$, $R^{14}$, $R^{15}$ and $R^{16}$ are each hydrogen.

Preference is furthermore given to those compounds of the formula I, wherein A is A38 and
$R^{13a}$ is a $C_1$-$C_4$alkyl, $C_2$-$C_4$alkenyl or $C_2$-$C_4$alkynyl group;
$R^{13b}$ is a $C_1$-$C_6$alkyl group; and
$R^{13c}$ is hydrogen or halogen, preferably hydrogen.

Preference is furthermore given to those compounds of the formula I, in which A is A1 and $R^6$ is phenyl, which is substituted in the para-position by halogen, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl) or $(Z)_pC$=$CR^{25}$, wherein said phenyl may be further substituted by 1 to 2 substituents, each independently selected from halogen, $C_{1-4}$ alkyl and $C_{1-4}$ haloalkyl, wherein Z is $C_{1-4}$ alkylene, p is 0 or 1, and $R^{25}$ is hydrogen, halogen, $C_{1-4}$alkyl, $C_{1-4}$haloalkyl, $C_{1-4}$ alkoxy($C_{1-4}$) alkyl, $C_{1-4}$ haloalkoxy($C_{1-4}$)alkyl or Si($C_{1-4}$ alkyl)$_3$.

Preference is furthermore given to those compounds of the formula I, in which A is A1 and $R^6$ is phenyl, which is substituted in the para-position by halogen, wherein said phenyl may be further substituted by 1 to 2 substituents, each independently selected from halogen, $C_{1-4}$ alkyl and $C_{1-4}$ haloalkyl; preferably said phenyl is only substituted in the para-position.

Preference is furthermore given to those compounds of the formula I, in which A is A1 and $R^6$ is phenyl, which is substituted in the para-position by C(H)=N—OH, C(H)=N—O($C_{1-6}$ alkyl), C($C_{1-6}$ alkyl)=N—OH or C($C_{1-6}$ alkyl)=N—O—($C_{1-6}$ alkyl); preferably said phenyl is only substituted in the para-position.

Preference is furthermore given to those compounds of the formula I, in which A is A1 and $R^6$ is phenyl, which is substituted in the para-position by $(Z)_pC$=$CR^{25}$, wherein said phenyl may be further substituted by 1 to 2 substituents, each independently selected from halogen, $C_{1-4}$ alkyl and $C_{1-4}$ haloalkyl, and wherein Z is $C_{1-4}$ alkylene, p is 0 or 1, and $R^{25}$ is hydrogen, halogen, $C_{1-4}$alkyl, $C_{1-4}$haloalkyl, $C_{1-4}$ alkoxy$(C_{1-4})$alkyl, $C_{1-4}$ haloalkoxy$(C_{1-4})$alkyl or $Si(C_{1-4}$ alkyl$)_3$; preferably said phenyl is only substituted in the para-position.

Preference is furthermore given to those compounds of the formula I, in which A is A1 and $R^6$ is phenyl, which is substituted in the para-position by $(Z)_pC\!\!=\!\!CR^{25}$, wherein said phenyl may be further substituted by 1 to 2 substituents, each independently selected from halogen, $C_{1-4}$ alkyl and $C_{1-4}$ haloalkyl, and wherein Z is $C_{1-4}$ alkylene, p is 0, and $R^{25}$ is hydrogen, $C_{1-4}$alkyl, $C_{1-4}$ haloalkyl, $C_{1-4}$ alkoxy$(C_{1-4})$alkyl, $C_{1-4}$ haloalkoxy$(C_{1-4})$alkyl; preferably said phenyl is only substituted in the para-position.

Preference is furthermore given to those compounds of the formula I, in which A is A1 and $R^6$ is a group of the form

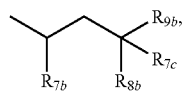

wherein $R_{7b}$ and $R_{7c}$ are independently of each other hydrogen, $C_1$-$C_3$alkyl or $C_1$-$C_3$haloalkyl, and $R_{8b}$ and $R_{9b}$ are independently of each other $C_1$-$C_3$alkyl or $C_1$-$C_3$haloalkyl.

Within said embodiment preference is furthermore given to those compounds, wherein $R_{7b}$ is hydrogen or $C_1$-$C_3$alkyl, $R_{7c}$ is hydrogen, and $R_{8b}$ and $R_{9b}$ are independently of each other $C_1$-$C_3$alkyl.

Within said embodiment preference is furthermore given to those compounds, wherein $R_{7b}$ is $C_1$-$C_3$alkyl, $R_{7c}$ is hydrogen, and $R_{8b}$ and $R_{9b}$ are independently of each other $C_1$-$C_3$alkyl.

Preference is furthermore given to those compounds of the formula I, in which A is A1 and $R^6$ is a $C_{3-8}$ cycloalkyl group, which may be substituted by 1 to 3 substituents, each independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each independently selected from $C_{1-4}$ alkyl, halogen, $C_{1-4}$alkoxy and $C_{1-4}$ haloalkoxy, and phenyl, which may itself be substituted by 1 to 5 independently selected halogen atoms.

Within said embodiment preference is furthermore given to those compounds, wherein $R^6$ is a $C_{3-8}$ cycloalkyl group, which is substituted by $C_{1-4}$ alkyl or $C_{3-6}$ cycloalkyl, wherein said $C_{3-6}$ cycloalkyl may itself be substituted by 1 to 3 substituents, each independently selected from $C_{1-4}$ alkyl.

Within said embodiment preference is furthermore given to those compounds, wherein $R^6$ is a $C_{3-8}$ cycloalkyl group, which is substituted by $C_{3-6}$ cycloalkyl, which may itself be substituted by 1 to 3 substituents, each independently selected from $C_{1-4}$ alkyl.

Within said embodiment preference is furthermore given to those compounds, wherein $R^6$ is a $C_{3-8}$ cycloalkyl group, which may be substituted by 1 to 3 substituents, each independently selected from halogen, $C_{1-4}$ alkyl and $C_{1-4}$ haloalkyl.

Within said embodiment preference is furthermore given to those compounds, wherein $R^6$ is a $C_{3-8}$ cycloalkyl group, which is substituted by 1 to 3 substituents, each independently selected from halogen, $C_{1-4}$ alkyl and $C_{1-4}$ haloalkyl.

Preference is furthermore given to those compounds of the formula I, in which A is A1 and $R^6$ is an aliphatic saturated or unsaturated group containing 3 to 13 carbon atoms and at least one silicon atom, wherein the aliphatic group may contain 1 to 3 heteroatoms, each heteroatom independently selected from oxygen, nitrogen and sulphur, and wherein the aliphatic group may be substituted by 1 to 4 independently selected halogen atoms.

Within said embodiment preference is furthermore given to those compounds, wherein $R^6$ is a group of the form

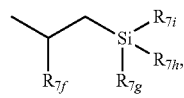

wherein $R_{7f}$ is hydrogen or $C_1$-$C_3$alkyl, and $R_{7g}$, $R_{7h}$ and $R_{7i}$ are independently of each other $C_1$-$C_3$alkyl.

Within said embodiment preference is furthermore given to those compounds, wherein $R_{7f}$ is hydrogen or $C_1$-$C_3$alkyl, and $R_{7g}$, $R_{7h}$ and $R_{7i}$ are each methyl.

Preference is furthermore given to those compounds of the formula I, in which A is A1 and $R^6$ is $(CR^aR^b)_n$-Cy-$(CR^cR^d)_n$—$Y_1$, wherein Cy is Cy17,

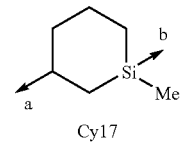

wherein "a" represents a bond to the moiety $(CR^aR^b)_m$ [and therefore that the arrow labelled "b" represents a bond to the moiety $(CR^cR^d)_n$].

Within said embodiment preference is furthermore given to those compounds, wherein $R^a$, $R^b$, $R^c$ and $R^d$ are each, independently, hydrogen or a $C_{1-4}$ alkyl group; $Y_1$ is hydrogen; and m and n are each independently 0, 1, 2 or 3;

Within said embodiment preference is furthermore given to those compounds, $Y_1$ is hydrogen; m is 0 and n is 1.

Preference is furthermore given to those compounds of the formula I, in which A is A2 and $R^6$ is a group of the form

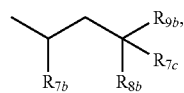

wherein $R_{7b}$ and $R_{7c}$ are independently of each other hydrogen, $C_1$-$C_3$alkyl or $C_1$-$C_3$haloalkyl, and $R_{8b}$ and $R_{9b}$ are independently of each other $C_1$-$C_3$alkyl or $C_1$-$C_3$haloalkyl.

Within said embodiment preference is furthermore given to those compounds, wherein $R_{7b}$ is hydrogen or $C_1$-$C_3$alkyl, $R_{7c}$ is hydrogen, and $R_{8b}$ and $R_{9b}$ are independently of each other $C_1$-$C_3$alkyl.

The compounds according to the present invention may be prepared according to the following reaction scheme (scheme 1), in which, unless otherwise stated, the definition of each variable is as defined above for a compound of formula (I).

Reaction Scheme 1:

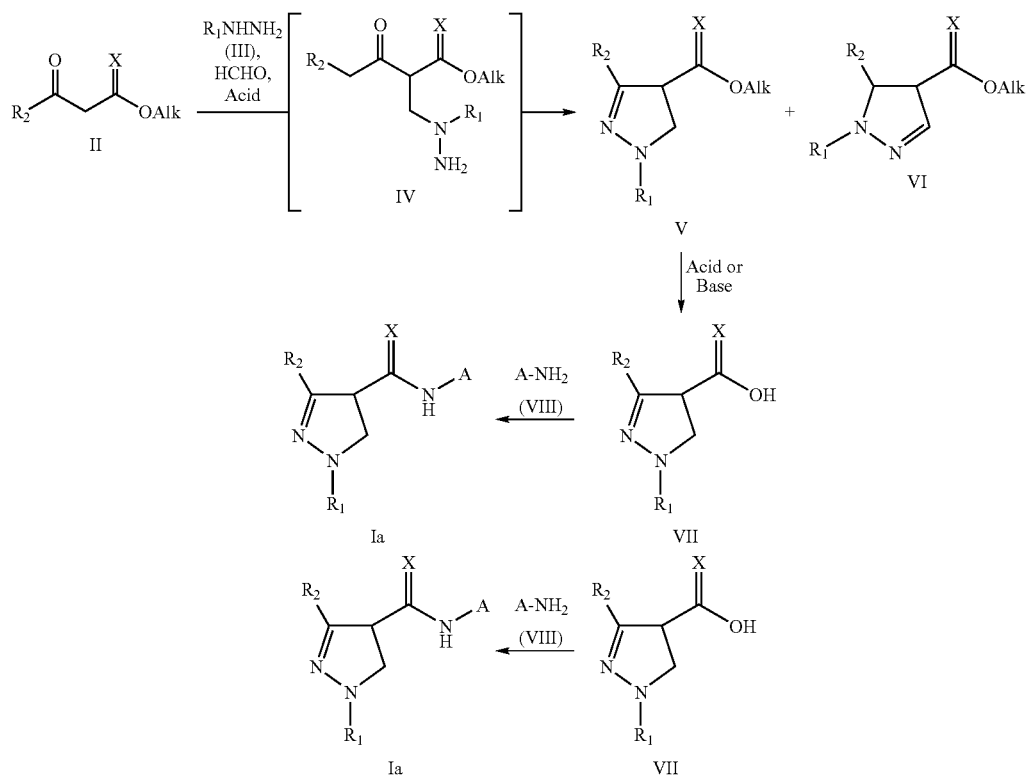

In compounds of formula II, IV, V and VI the radical "Alk" stands for an alkyl group, preferably $C_{1-6}$alkyl.

Compounds of formula Ia may be obtained by reacting a carboxylic acid of formula VII or an activated form of this carboxylic acid VII, like an acid chloride, a symmetrical or mixed acid anhydride or other kinds of activated esters, with an amine of formula VII. The reaction of compounds of formula VII with compound of formula VIII to form compounds of formula Ia corresponds to a standard amidation and is preferably carried out in the presence of a base.

Starting from compounds of formula Ia, compounds of formula I, wherein $R_3$ is different from hydrogen can be prepared by using suitable known standard methods. For example, compounds of formula I, wherein $R_3$ is $C_{1-4}$ alkyl can be prepared from compounds of formula Ia by lithiation; compounds of formula I, wherein $R_3$ is halogen can be prepared from compounds of formula Ia by halogenation; and compounds of formula I, wherein $R_3$ is cyano can be prepared from compounds of formula Ia by cyanide-substitution.

Compounds of formula VII may be obtained by hydrolysis of an carboxylic acid ester of formula V. The reaction of compounds of formula V to compounds VII corresponds to a standard ester cleavage and is preferably carried out in the presence of an acid or a base.

Compounds of formula V may be obtained together with compounds of formula VI by a novel three-component condensation of a β-ketoester or a β-ketothioester of formula II, a hydrazine of formula III and formaldehyde. The reaction of compounds of formula II with compounds of formula III and formaldehyde to form compounds of formula V and compounds of formula VI is advantageously carried out in the presence of proton acid, like hydrochloric acid or sulfuric acid, or in the presence of a Lewis acid, like boron trifluoride ethyl etherate or titanium tetrachloride. The reaction undergoes an intermediate of formula IV. The ratio between compounds of formula V and VI depends on the substituent $R_1$ in the hydrazine of formula III and on the substituent $R_2$ in the β-ketoester or β-ketothioester of formula II.

Compounds of formula II and III are known and commercially available or can be prepared easily from commercial available precursors according to generally known methods.

Amines of formula VIII are either known, for example, from EP-0-824-099, WO 93/11117, International patent application no. PCT/EP2005/006688 and European patent application no. 05006382.5, or they can be prepared according to generally known conversion methods.

For preparing all further compounds of the formula I functionalized according to the definitions of $R_1$, $R_2$, $R_3$, $R_4$, X and A, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The reactions to give compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at room temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds I and, where appropriate, the tautomers thereof, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisams, such as fungi, bacteria or viruses.

The invention relates to a method of controlling or preventing infestation of useful plants by phytopathogenic microorganisms, wherein a compound of formula I is applied as acitve ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: *Fungi imperfecti* (e.g. *Botrytis, Pyricularia, Helminthosporium, Fusarium, Septoria, Cercospora* and *Alternaria*) and *Basidiomycetes* (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Good activity has been observed against Asian soybean rust (*Phakopsora pachyrhizi*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); *lauraceae* (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I ® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example for a truncated toxin is a truncated CryIA(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and butterflies (*Lepidoptera*).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Boligard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Btl 1 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.
4. MON 863 Maize from Monsanto Europe S. A. 270-272 Avenue de Tervuren, B-1150 Brussels, Belgium, registration number C/DE/02/9. MON 863 expresses a CryIIIB (b1) toxin and has resistance to certain Coleoptera insects.

5. IPC 531 Cotton from Monsanto Europe S. A. 270-272 Avenue de Tervuren, B-1150 Brussels, Belgium, registration number C/ES/96102.
6. 1507 Maize from Pioneer Overseas Corporation, Avenue Tedesco, 7 B-1160 Brussels, Belgium, registration number C/NUOO/10. Genetically modified maize for the expression of the protein Cry1F for achieving resistance to certain *Lepidoptera* insects and of the PAT protein for achieving tolerance to the herbicide glufosinate ammonium.
7. NK603×MON 810 Maize from Monsanto Europe S. A. 270-272 Avenue de Tervuren, B-1150 Brussels, Belgium, registration number C/GB/O$_2$/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain *Lepidoptera*, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Surprisingly, it has now been found that the compounds of formula I, or a pharmaceutical salt thereof, described above have also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula I in the manufacture of a medicament for use in the treatment and/or prevention of microbial infection in an animal. There is also provided the use of a compound of formula I as a pharmaceutical agent. There is also provided the use of a compound of formula I as an antimicrobial agent in the treatment of an animal. According to the present invention there is also provided a pharmaceutical composition comprising as an active ingredient a compound of formula I, or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula I are effective against various microbial species able to cause a microbial infection in an animal. Examples of such microbial species are those causing Aspergillosis such as *Aspergillus fumigatus, A. flavus, A. terrus, A. nidulans* and *A. niger*, those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 1-methyl-3-trifluoromethyl-4,5-dihydro-1H-pyrazole-4-carboxylic acid [2-(1,3-dimethyl-butyl)-thiophen-3-yl]-amide (Compound No. 1.188)

a) Preparation of 1-methyl-3-trifluoromethyl-4,5-dihydro-1H-pyrazole-4-carboxylic acid ethyl ester Ethyl 4,4,4-trifluoroacetoacetate (120 g, 0.65 mol) was dissolved in 650 ml of ethanol and the solution was cooled down to 0° C. A 37% aqueous solution of formaldehyde (53 g, 0.65 mol) was added and the mixture was stirred for 15 minutes at 0° C. Methylhydrazine (30 g, 0.65 mol) was added and the reaction mixture was heated to reflux. After reaching the reflux temperature, 2.5 ml of concentrated hydrochloric acid were added, and refluxing was continued for 16 h. Subsequently, the mixture was cooled down and the solvent was removed in vacuo. The remainder was taken up in water and extracted with ethyl acetate. The combined organic layer was washed with water, dried over magnesium sulfate and evaporated. The remaining oil was purified by silica gel chromatography using ethyl acetate and hexane as eluents, yielding 90 g of 1-methyl-3-trifluoromethyl-4,5-dihydro-1H-pyrazole-4-carboxylic acid ethyl ester.

b) Preparation of 1-methyl-3-trifluoromethyl-4,5-dihydro-1H-pyrazole-4-carboxylic acid 1-Methyl-3-trifluoromethyl-4,5-dihydro-1H-pyrazole-4-carboxylic acid ethyl ester (20 g, 90 mmol) was dissolved in 400 ml of dioxan. 400 ml of a 1 N aqueous sodium hydroxide solution (0.4 mol) were added and the reaction mixture was stirred for 2 h at room temperature. Subsequently the mixture was acidified with concentrated hydrochloric acid (pH 2). The dioxan was removed in vacuo, the residue was extracted with ethyl acetate. The combined organic layer was washed with brine, dried over magnesium sulfate and evaporated, delivering 15 g of 1-methyl-3-trifluoromethyl-4,5-dihydro-1H-pyrazole-4-carboxylic acid, which could be directly used in the next step without further purification.

c) 1-methyl-3-trifluoromethyl-4,5-dihydro-1H-pyrazole-4-carboxylic acid (2.5 g, 13 mmol) was dissolved in 20 ml of dichloromethane containing 5 drops of N,N-dimethylformamide. A solution of oxalyl chloride (1.8 g, 14 mmol) in 5 ml of dichloromethane was added dropwise at room temperature. This mixture was stirred for 2 h at the same temperature and subsequently slowly added to a mixture of 2-(1,3-dimethyl-butyl)-thiophen-3-ylamine (2.3 g, 13 mmol) and triethylamine (2.0 g, 20 mmol) in 20 ml of dichloromethane. After stirring the reaction mixture for 16 h at room temperature, it was poured on ice and extracted with dichloromethane. The combined organic layer was washed with brine, dried over magnesium sulfate and evaporated. The remaining oil was purified by silica gel chromatography using ethyl acetate and hexane as eluents, giving 2.2 g of 1-methyl-3-trifluoromethyl-4,5-dihydro-1H-pyrazole-4-carboxylic acid [2-(1,3-dimethyl-butyl)-thiophen-3-yl]-amide (Compound No. 1.188).

Example P1

Preparation of 3-difluoromethyl-1-methyl-4,5-dihydro-1H-pyrazole-4-carboxylic acid (4'-chloro-biphenyl-2-yl)-amide (Compound No. 1.006)

a) Preparation of 3-difluoromethyl-1-methyl-4,5-dihydro-1H-pyrazole-4-carboxylic acid ethyl ester Ethyl 4,4-difluoroacetoacetate (5.0 g, 30 mmol) was dissolved in 35 ml of ethanol and the solution was cooled down to 0° C. A 37% aqueous solution of formaldehyde (2.5 g, 30 mmol) was added and the mixture was stirred for 15 minutes at 0° C. Methylhydrazine (1.4 g, 30 mmol) was added and the reaction mixture was heated to reflux. After reaching the reflux temperature, 0.5 ml of concentrated hydrochloric acid were added, and refluxing was continued for 16 h. Subsequently, the mixture was cooled down and the solvent was removed in vacuo. The remainder was taken up in water and extracted with ethyl acetate. The combined organic layer was washed with water, dried over magnesium sulfate and evaporated. The remaining oil was purified by silica gel chromatography using ethyl acetate and hexane as eluents, yielding 1.5 g of 3-difluoromethyl-1-methyl-4,5-dihydro-1H-pyrazole-4-carboxylic acid ethyl ester.

b) Preparation of 3-difluoromethyl-1-methyl-4,5-dihydro-1H-pyrazole-4-carboxylic acid 3-Difluoromethyl-1-methyl-4,5-dihydro-1H-pyrazole-4-carboxylic acid ethyl ester (0.15 g, 0.7 mmol) was dissolved in 2 ml of dioxan. 1.5 ml of a 1 N aqueous sodium hydroxide solution (1.5 mmol) were added and the reaction mixture was stirred for 2 h at room temperature. Subsequently the mixture was acidified with concentrated hydrochloric acid (pH 2). The dioxan was removed in vacuo, the residue was extracted with ethyl acetate. The combined organic layer was washed with brine, dried over magnesium sulfate and evaporated, delivering 0.1 g of 3-difluoromethyl-1-methyl-4,5-dihydro-1H-pyrazole-4-carboxylic acid, which could be directly used in the next step without further purification.

c) 3-Difluoromethyl-1-methyl-4,5-dihydro-1H-pyrazole-4-carboxylic acid (0.1 g, 0.5 mmol) was dissolved in 2 ml of dichloromethane containing 1 drop of N,N-dimethylformamide. A solution of oxalyl chloride (78 mg, 0.6 mmol) in 2 ml of dichloromethane was added dropwise at room temperature. This mixture was stirred for 2 h at the same temperature and subsequently slowly added to a mixture of 4'-chloro-biphenyl-2-ylamine (0.11 g, 0.5 mmol) and triethylamine (85 mg, 0.8 mmol) in 2 ml of dichloromethane. After stirring the reaction mixture for 16 h at room temperature, it was poured on ice and extracted with dichloromethane. The combined organic layer was washed with brine, dried over magnesium sulfate and evaporated. The remaining oil was purified by silica gel chromatography using ethyl acetate and hexane as eluents, giving 40 mg of 3-difluoromethyl-1-methyl-4,5-dihydro-1H-pyrazole-4-carboxylic acid (4'-chloro-biphenyl-2-yl)-amide (Compound No. 1.006).

The compounds in Tables 1 to 7 below illustrate compounds of the invention.

Table W represents Table 1 (when W is 1), represents Table 2 (when W is 2), represents Table 3 (when W is 3), represents Table 4 (when W is 4), represents Table 5 (when W is 5), represents Table 6 (when W is 6) and represents Table 7 (when W is 7).

TABLE W

| Compound No. | R$_4$ | A | X |
|---|---|---|---|
| W.001 | H | (2-phenyl-phenyl) | O |
| W.002 | H | (4'-fluoro-biphenyl-2-yl) | O |
| W.003 | H | (4'-fluoro-biphenyl-2-yl) | S |
| W.004 | CH$_2$C≡CH | (4'-fluoro-biphenyl-2-yl) | O |
| W.005 | CH=C=CH$_2$ | (3'-fluoro-biphenyl-2-yl) | O |

TABLE W-continued
| Compound No. | R4 | A | X |
|---|---|---|---|
| W.006 | H | 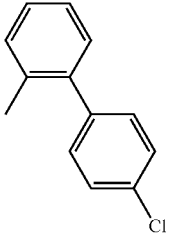 | O |
| W.007 | H | 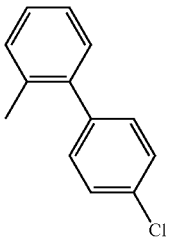 | S |
| W.008 | CH₂C≡CH | 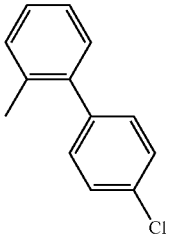 | O |
| W.009 | CH=C=CH₂ | 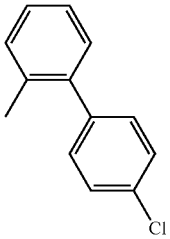 | O |
| W.010 | H | 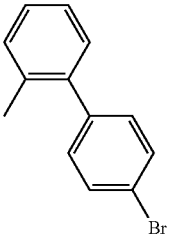 | O |
| W.011 | H | 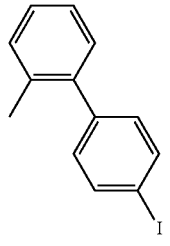 | O |
TABLE W-continued
| Compound No. | R4 | A | X |
|---|---|---|---|
| W.012 | H | 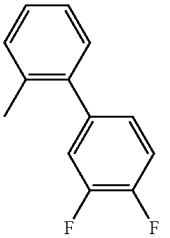 | O |
| W.013 | H | 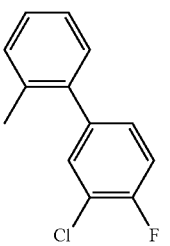 | O |
| W.014 | H | 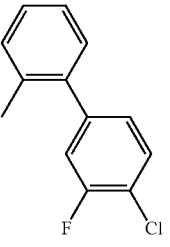 | O |
| W.015 | H | 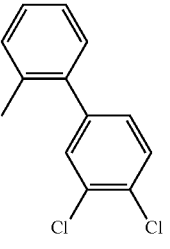 | O |
| W.016 | H | 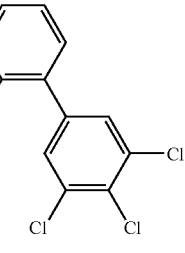 | O |
| W.017 | H | 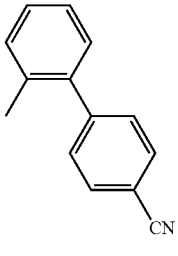 | O |

TABLE W-continued
| Compound No. | R4 | A | X |
|---|---|---|---|
| W.018 | H | 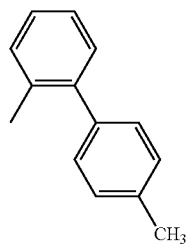 | O |
| W.019 | H | 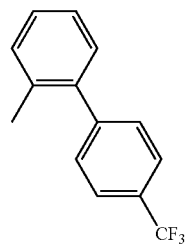 | O |
| W.020 | H | 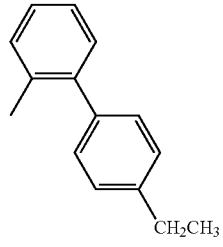 | O |
| W.021 | H | 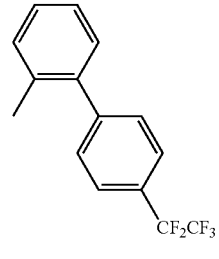 | O |
| W.022 | H | 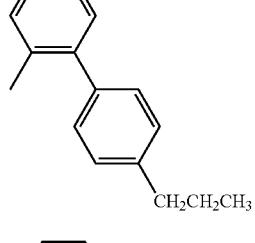 | O |
| W.023 | H | 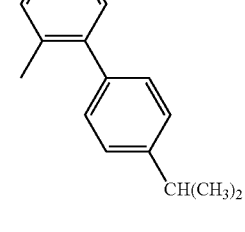 | O |
| W.024 | H | 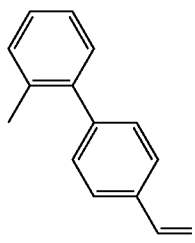 | O |
| W.025 | H | 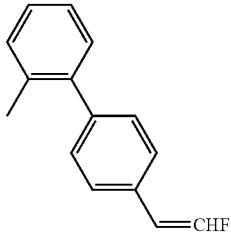 | O |
| W.026 | H | 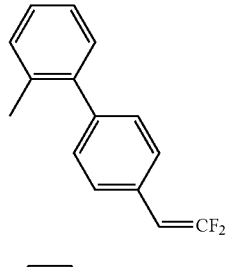 | O |
| W.027 | H | 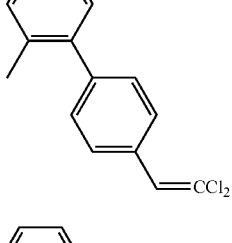 | O |
| W.028 | H | 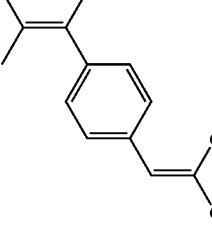 | O |
| W.029 | H | 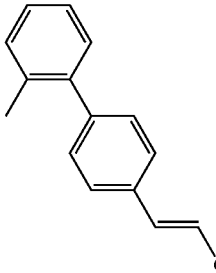 | O |

TABLE W-continued
| Compound No. | R₄ | A | X |
|---|---|---|---|
| W.030 | H | 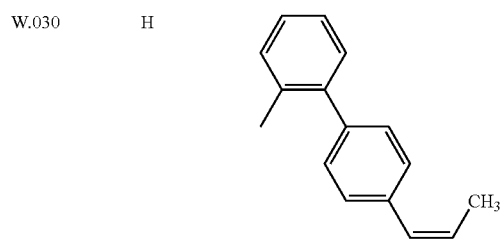 | O |
| W.031 | H | 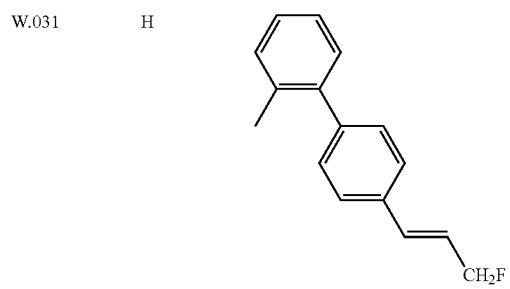 | O |
| W.032 | H | 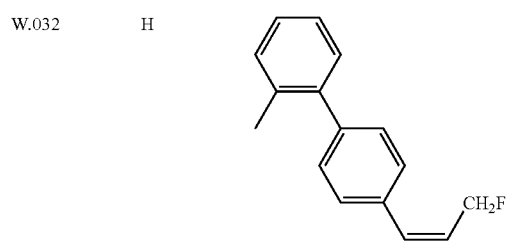 | O |
| W.033 | H | 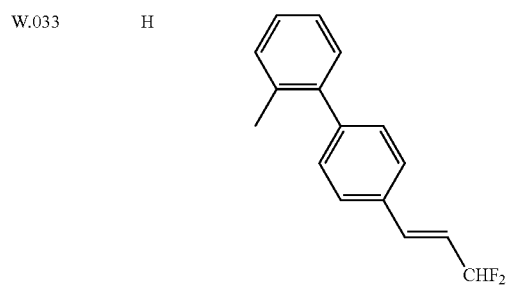 | O |
| W.034 | H | 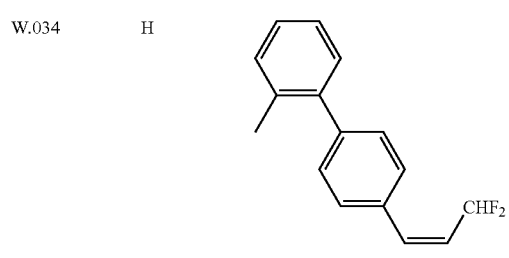 | O |
| W.035 | H | 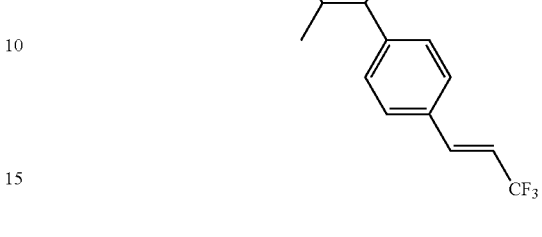 | O |
| W.036 | H | 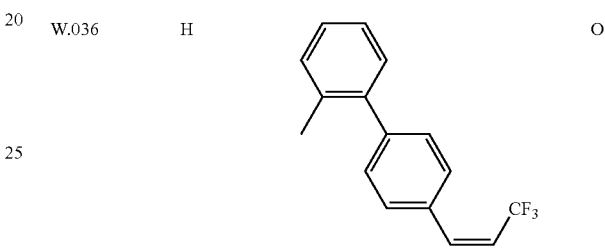 | O |
| W.037 | H | 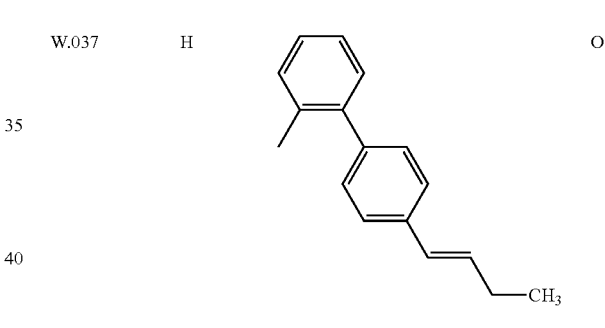 | O |
| W.038 | H | 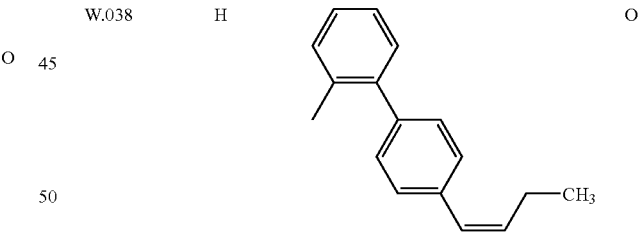 | O |
| W.039 | H | 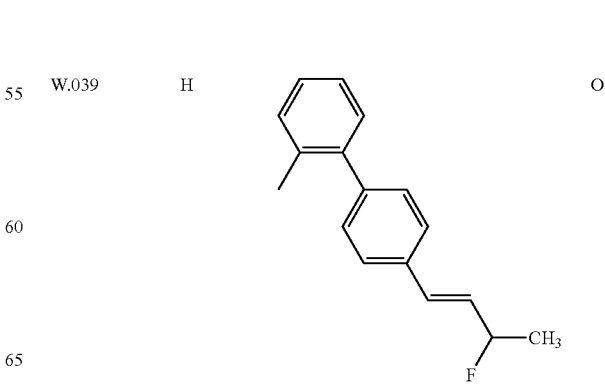 | O |

TABLE W-continued

| Compound No. | R₄ | A | X |
|---|---|---|---|
| W.040 | H | (2-methylbiphenyl-4-yl)-CH=CH-CHF-CH₃ (Z) | O |
| W.041 | H | (2-methylbiphenyl-4-yl)-CH=CH-CF₂-CH₃ (E) | O |
| W.042 | H | (2-methylbiphenyl-4-yl)-CH=CH-CF₂-CH₃ (Z) | O |
| W.043 | H | (2-methylbiphenyl-4-yl)-CH=CH-CF₂-CF₃ (E) | O |
| W.044 | H | (2-methylbiphenyl-4-yl)-CH=CH-CF₂-CF₃ (Z) | O |
| W.045 | H | (2-methylbiphenyl-4-yl)-CH=CH-CH(CH₃)₂ (E) | O |
| W.046 | H | (2-methylbiphenyl-4-yl)-CH=CH-CH(CH₃)₂ (Z) | O |
| W.047 | H | (2-methylbiphenyl-4-yl)-CH=CH-CF(CH₃)₂ (E) | O |
| W.048 | H | (2-methylbiphenyl-4-yl)-CH=CH-CF(CH₃)₂ (Z) | O |
| W.049 | H | (2-methylbiphenyl-4-yl)-CH=CH-C(CH₃)₂(OCH₃) (E) | O |

TABLE W-continued
| Compound No. | R4 | A | X |
|---|---|---|---|
| W.050 | H | 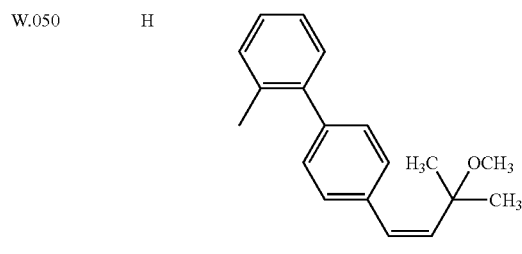 | O |
| W.051 | H | 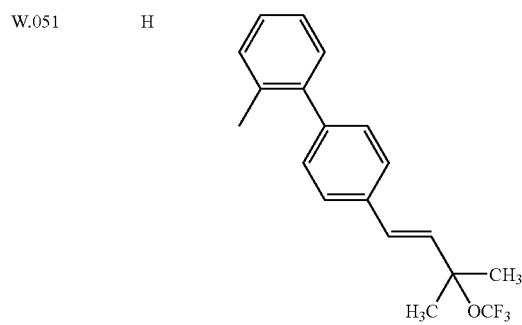 | O |
| W.052 | H | 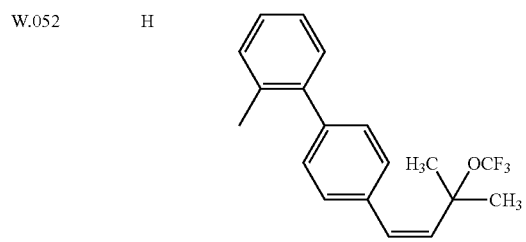 | O |
| W.053 | H | 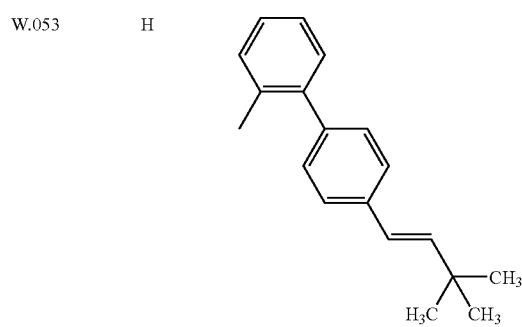 | O |
| W.054 | H | 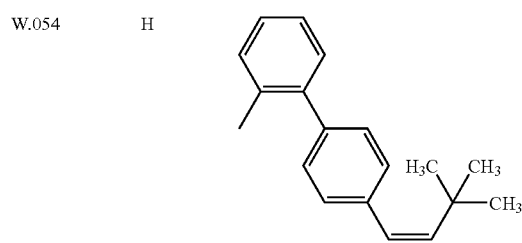 | O |
| W.055 | H | 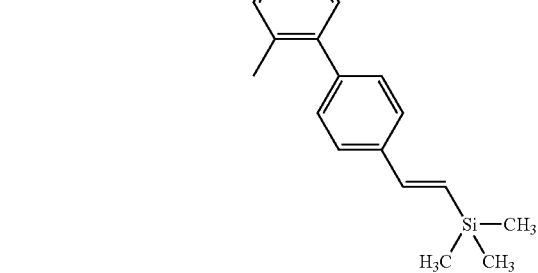 | O |
| W.056 | H | 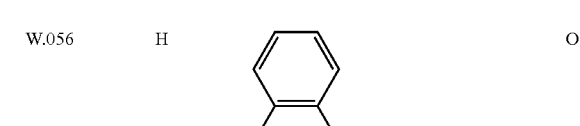 | O |
| W.057 | H | 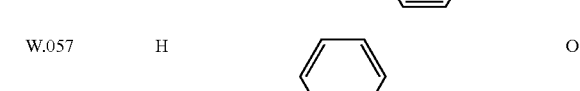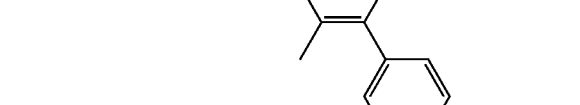 | O |
| W.058 | H | 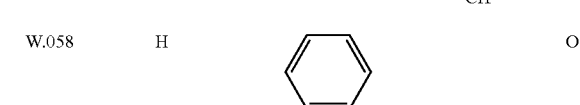 | O |
| W.059 | H | 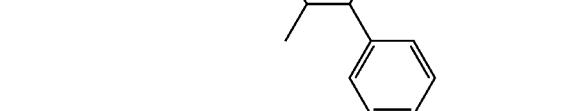 | O |

TABLE W-continued
| Compound No. | R4 | A | X |
|---|---|---|---|
| W.060 | H | 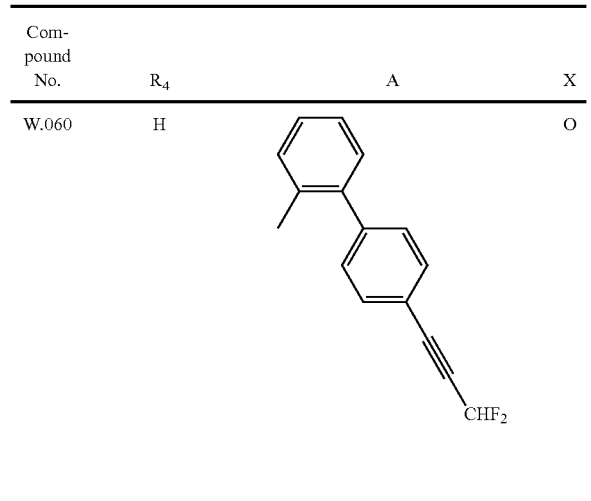 | O |
| W.061 | H | 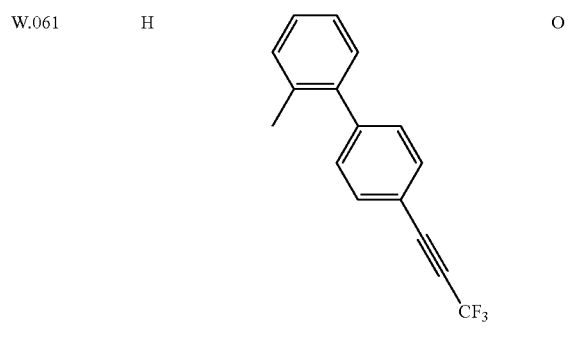 | O |
| W.062 | H | 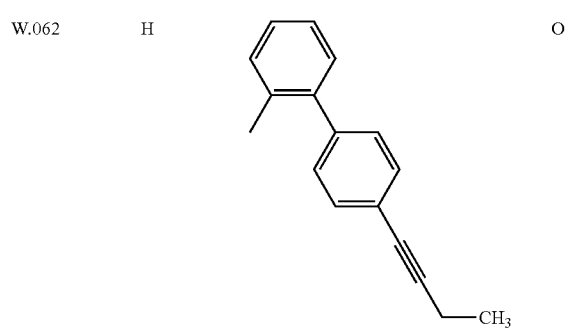 | O |
| W.063 | H | 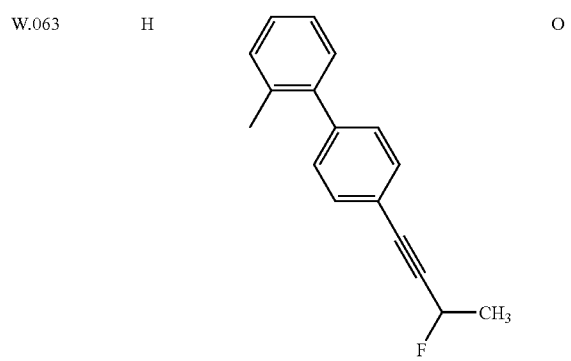 | O |
TABLE W-continued
| Compound No. | R4 | A | X |
|---|---|---|---|
| W.064 | H | 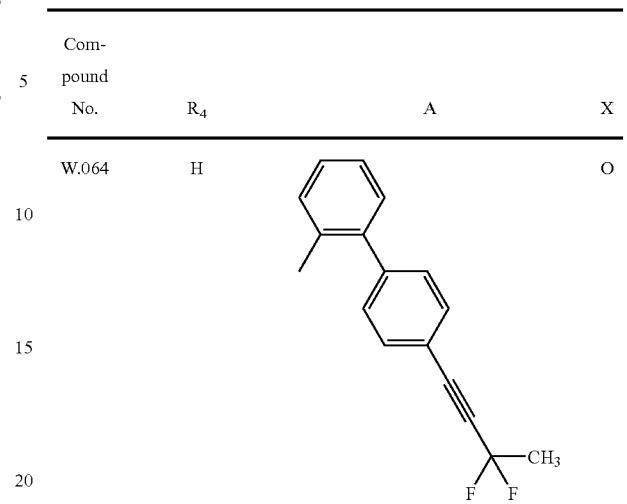 | O |
| W.065 | H | 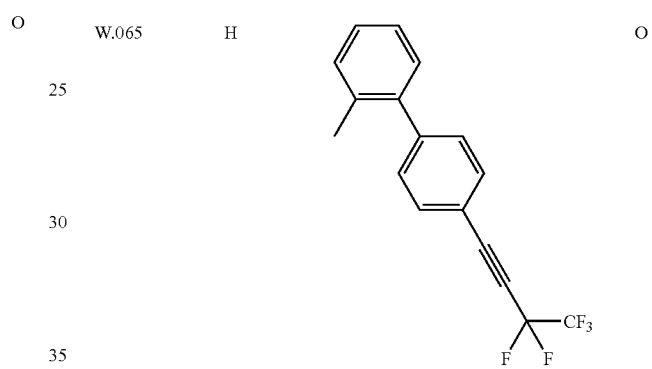 | O |
| W.066 | H | 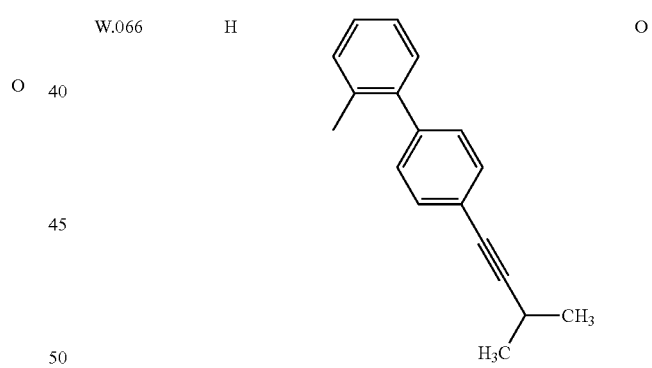 | O |
| W.067 | H | 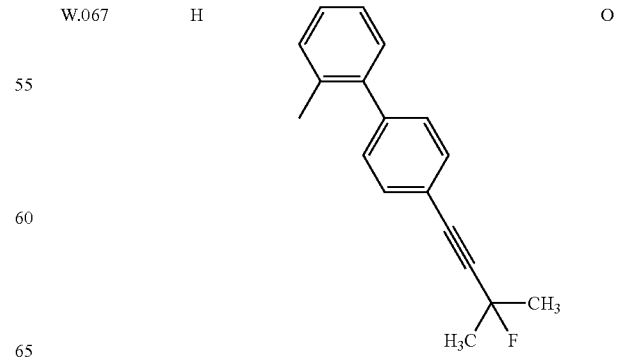 | O |

TABLE W-continued

| Compound No. | R₄ | A | X |
|---|---|---|---|
| W.068 | H | 2-methylbiphenyl-4-yl-C≡C-C(CH₃)₂-OCH₃ | O |
| W.069 | H | 2-methylbiphenyl-4-yl-C≡C-C(CH₃)₂-OCF₃ | O |
| W.070 | H | 2-methylbiphenyl-4-yl-C≡C-C(CH₃)₃ | O |
| W.071 | H | 2-methylbiphenyl-4-yl-C≡C-Si(CH₃)₃ | O |
| W.072 | H | 2-methylbiphenyl-4-yl-CH=N-OCH₃ | O |
| W.073 | H | 2-methylbiphenyl-4-yl-CH=N-OCF₃ | O |
| W.074 | H | 2-methylbiphenyl-4-yl-CH=N-OCH₂CH₃ | O |
| W.075 | H | 2-methylbiphenyl-4-yl-CH=N-N(CH₃)₂ | O |
| W.076 | H | 2-methylbiphenyl-4-yl-C(CH₃)=N-OCH₃ | O |

TABLE W-continued

| Compound No. | R₄ | A | X |
|---|---|---|---|
| W.077 | H | 2'-methyl-biphenyl-4-yl with C(CH₃)=N-OCF₃ substituent | O |
| W.078 | H | 2'-methyl-biphenyl-4-yl with C(CH₃)=N-OCH₂CH₃ substituent | O |
| W.079 | H | 2'-methyl-biphenyl-4-yl with C(CH₃)=N-N(CH₃)₂ substituent | O |
| W.080 | H | 2'-methyl-4-methoxy-biphenyl | O |
| W.081 | H | 2'-methyl-4-trifluoromethoxy-biphenyl | O |
| W.082 | H | 2-methyl-4'-methylthio-biphenyl | O |
| W.083 | H | 2-methyl-4'-trifluoromethylthio-biphenyl | O |
| W.084 | H | 2-methylphenyl | O |
| W.085 | H | 2-methyl-3-tert-butylphenyl (with additional CH₃) | O |
| W.086 | H | 2-ethylphenyl | O |
| W.087 | H | 2-ethyl-3-tert-butyl-phenyl (with additional CH₃) | O |
| W.088 | H | 2-propylphenyl | O |

TABLE W-continued

| Compound No. | R$_4$ | A | X |
|---|---|---|---|
| W.089 | H | 2-methyl-6-(tert-butyl)phenyl with propyl | O |
| W.090 | H | 2-methyl-6-isopropylphenyl | O |
| W.091 | H | 2,3-dimethyl-6-isopropylphenyl | O |
| W.092 | H | 2-methyl-6-(sec-butyl)phenyl | O |
| W.093 | H | 2,3-dimethyl-6-(sec-butyl)phenyl | O |
| W.094 | H | 2-methyl-6-(tert-butyl)phenyl | O |
| W.095 | H | 2,3-dimethyl-6-(tert-butyl)phenyl | O |
| W.096 | H | 2-methyl-6-(pentan-2-yl)phenyl | O |
| W.097 | H | 2-methyl-6-(2,4-dimethylpentan-3-yl)phenyl | O |
| W.098 | H | 2-methyl-6-(2,4-dimethylpentan-3-yl)phenyl | S |
| W.099 | CH$_2$C≡CH | 2-methyl-6-(2,4-dimethylpentan-3-yl)phenyl | O |
| W.100 | CH=C=CH$_2$ | 2-methyl-6-(2,4-dimethylpentan-3-yl)phenyl | O |
| W.101 | H | 2-methyl-6-(2,2-dimethyl-hexan-3-yl)phenyl | O |
| W.102 | H | 2-methyl-6-(3-methylpentan-2-yl)phenyl | O |
| W.103 | H | 2-methyl-6-(2-methylpentan-3-yl)phenyl | O |

TABLE W-continued

| Compound No. | R4 | A | X |
|---|---|---|---|
| W.104 | H | 2-methylphenyl-CH(CH3)-CH2-CH(CH3)2 | O |
| W.105 | H | 2-methylphenyl-CH2CH2-cyclopropyl | O |
| W.106 | H | 2-methylphenyl-CH(CH3)-CH2-cyclopropyl | O |
| W.107 | H | 2-methylphenyl-CH2CH2-Si(CH3)3 | O |
| W.108 | H | 2-methylphenyl-CH(CH3)-CH2-Si(CH3)3 | O |
| W.109 | H | 2-methylphenyl-(trans-cyclopropyl)-C(CH3)3 | O |
| W.110 | H | 2-methylphenyl-(cis-cyclopropyl)-C(CH3)3 | O |
| W.111 | H | 2-methylphenyl-(trans-cyclopropyl)-Si(CH3)3 | O |
| W.112 | H | 2-methylphenyl-(cis-cyclopropyl)-Si(CH3)3 | O |
| W.113 | H | 2-methylphenyl-(trans-cyclopropyl)-cyclopropyl | O |
| W.114 | H | 2-methylphenyl-(cis-cyclopropyl)-cyclopropyl | O |
| W.115 | H | 2-methylphenyl-cyclopropyl(CH3)-cyclopropyl | O |
| W.116 | H | 2-methylphenyl-cyclopropyl(CH3)-cyclopropyl | O |
| W.117 | H | 2-methylphenyl-cyclopropyl-C(CH3)(cyclopropyl) | O |

TABLE W-continued
| Compound No. | R4 | A | X |
|---|---|---|---|
| W.118 | H | 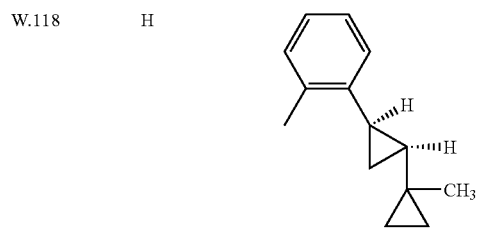 | O |
| W.119 | H | 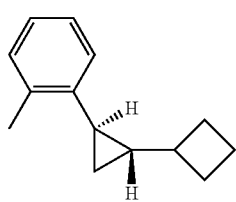 | O |
| W.120 | H | 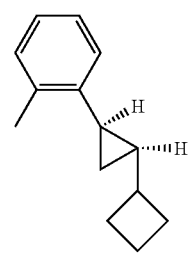 | O |
| W.121 | H | 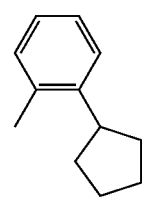 | O |
| W.122 | H | 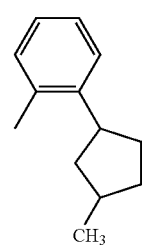 | O |
| W.123 | H | 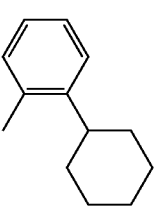 | O |
| W.124 | H | 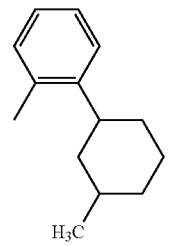 | O |
| W.125 | H | 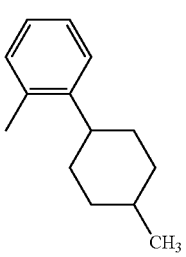 | O |
| W.126 | H | 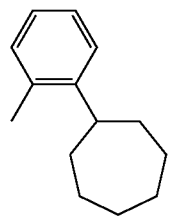 | O |
| W.127 | H | 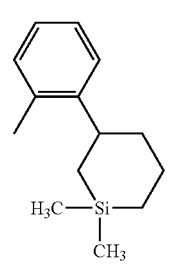 | O |
| W.128 | H | 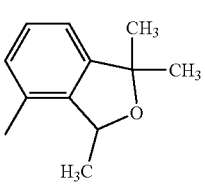 | O |
| W.129 | H | 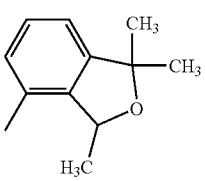 | S |
| W.130 | CH$_2$C≡CH | 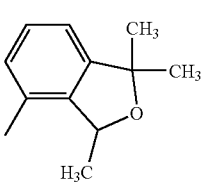 | O |

TABLE W-continued

| Compound No. | R4 | A | X |
|---|---|---|---|
| W.131 | CH=C=CH2 | [2,2,4-trimethyl-1,3-dihydroisobenzofuran with CH3 at 1-position] | O |
| W.132 | H | [1,1,3-trimethyl-4-methylindane] | O |
| W.133 | H | [1,4-dimethyl-7-oxabicyclic aromatic structure] | O |
| W.134 | H | [methyl-benzonorbornene] | O |
| W.135 | H | [methyl-benzonorbornene with CH3 on bridge] | O |
| W.136 | H | [methyl-benzonorbornene with CH3] | O |
| W.137 | H | [methyl-benzonorbornene with FH2C] | O |
| W.138 | H | [methyl-benzonorbornene with CH2F] | O |
| W.139 | H | [methyl-benzonorbornene with F3C] | O |

TABLE W-continued

| Compound No. | R4 | A | X |
|---|---|---|---|
| W.140 | H | [methyl-benzonorbornene with CF3] | O |
| W.141 | H | [methyl-benzonorbornene with ethyl CH3] | O |
| W.142 | H | [methyl-benzonorbornene with ethyl CH3] | O |
| W.143 | H | [methyl-benzonorbornene with propyl H3C] | O |
| W.144 | H | [methyl-benzonorbornene with propyl CH3] | O |
| W.145 | H | [methyl-benzonorbornene with isopropyl] | O |
| W.146 | H | [methyl-benzonorbornene with isobutyl] | O |

TABLE W-continued
| Compound No. | R₄ | A | X |
|---|---|---|---|
| W.147 | H | 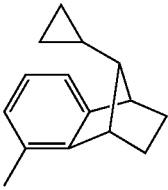 | O |
| W.148 | H | 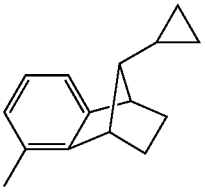 | O |
| W.149 | H | 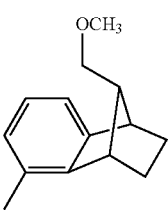 | O |
| W.150 | H | 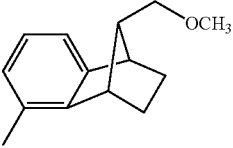 | O |
| W.151 | H | 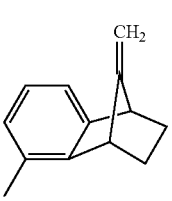 | O |
| W.152 | H | 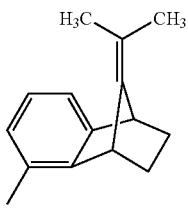 | O |
| W.153 | H | 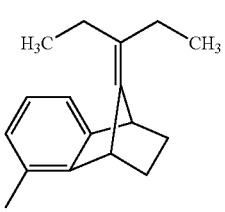 | O |
| W.154 | H | 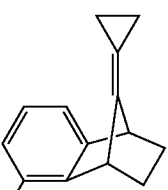 | O |
| W.155 | H | 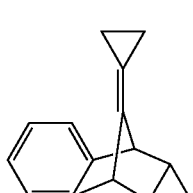 | O |
| W.156 | H | 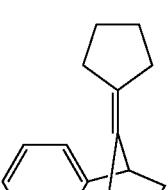 | O |
| W.157 | H | 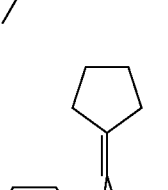 | O |
| W.158 | H | 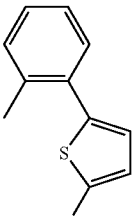 | O |
| W.159 | H | 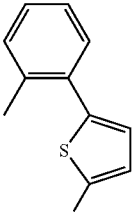 | O |

TABLE W-continued
| Compound No. | R4 | A | X |
|---|---|---|---|
| W.160 | H | 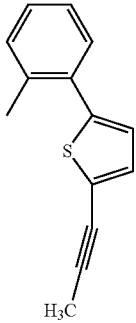 | O |
| W.161 | H | 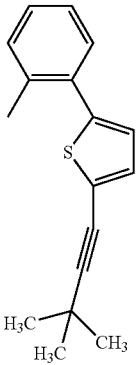 | O |
| W.162 | H | 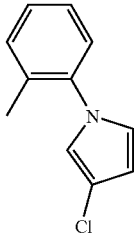 | O |
| W.163 | H | 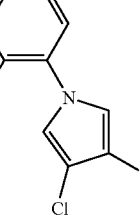 | O |
| W.164 | H | 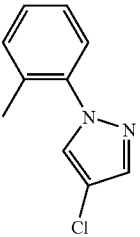 | O |
| W.165 | H | 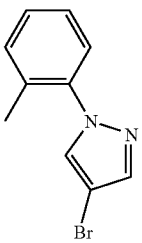 | O |
| W.166 | H | 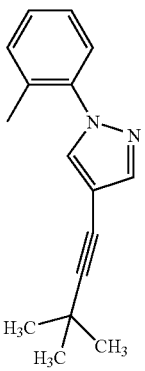 | O |
| W.167 | H | 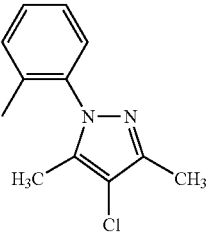 | O |
| W.168 | H | 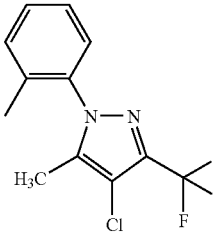 | O |
| W.169 | H | 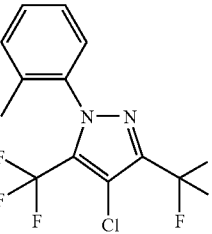 | O |

TABLE W-continued
| Compound No. | R4 | A | X |
|---|---|---|---|
| W.170 | H | 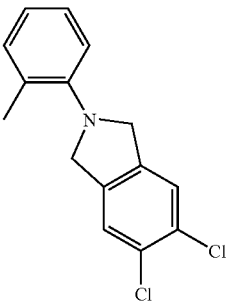 | O |
| W.171 | H | 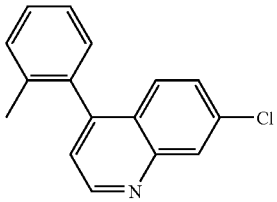 | O |
| W.172 | H | 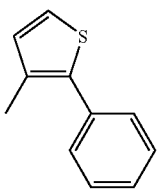 | O |
| W.173 | H | 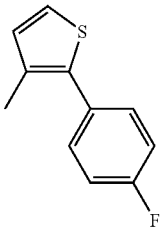 | O |
| W.174 | H | 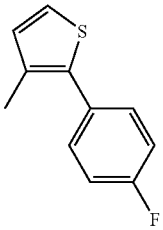 | S |
| W.175 | CH$_2$C≡CH | 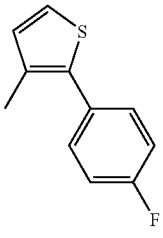 | O |
TABLE W-continued
| Compound No. | R4 | A | X |
|---|---|---|---|
| W.176 | CH=C=CH$_2$ | 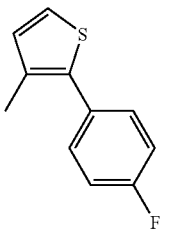 | O |
| W.177 | H | 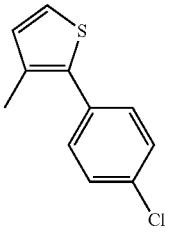 | O |
| W.178 | H | 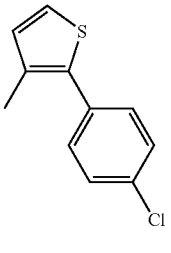 | S |
| W.179 | CH$_2$C≡CH | 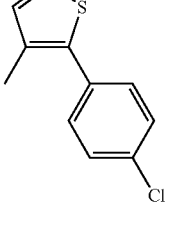 | O |
| W.180 | CH=C=CH$_2$ | 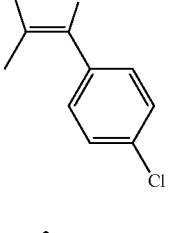 | O |
| W.181 | H | 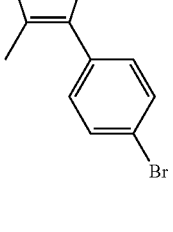 | O |

TABLE W-continued
| Compound No. | R4 | A | X |
|---|---|---|---|
| W.182 | H | 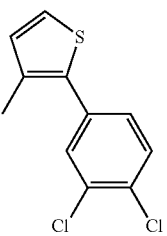 | O |
| W.183 | H | 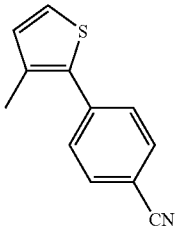 | O |
| W.184 | H | 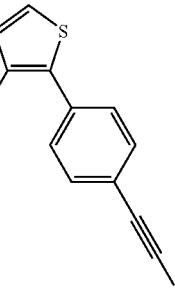 | O |
| W.185 | H | 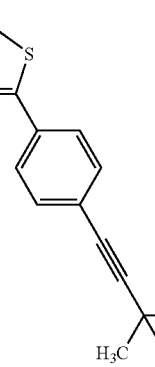 | O |
| W.186 | H | 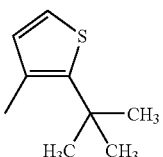 | O |
| W.187 | H | 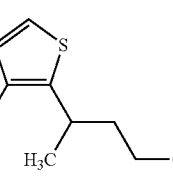 | O |
| W.188 | H | 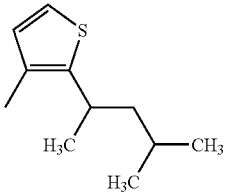 | O |
| W.189 | H | 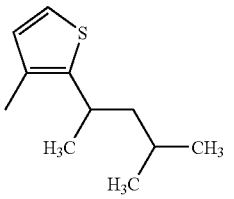 | S |
| W.190 | CH$_2$=CH | 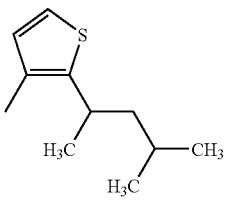 | O |
| W.191 | CH=CH$_2$ | 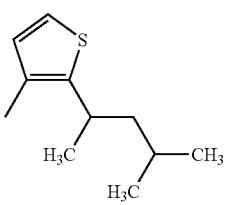 | O |
| W.192 | H | 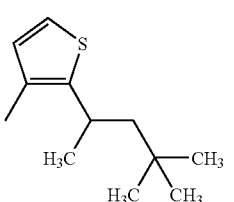 | O |
| W.193 | H | 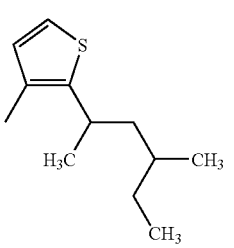 | O |
| W.194 | H | 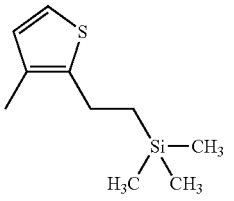 | O |

TABLE W-continued

| Compound No. | R₄ | A | X |
|---|---|---|---|
| W.195 | H | 2-(3-methylthiophen-2-yl)propyl-trimethylsilane | O |
| W.196 | H | 2-(3-methylthiophen-2-yl)-trans-cyclopropyl-cyclopropane | O |
| W.197 | H | 2-(3-methylthiophen-2-yl)-cis-cyclopropyl-cyclopropane | O |
| W.198 | H | 2-(3-methylthiophen-2-yl)-trans-(1-methylcyclopropyl)cyclopropane | O |
| W.199 | H | 2-(3-methylthiophen-2-yl)-cis-(1-methylcyclopropyl)cyclopropane | O |
| W.200 | H | 2-(3-methylcyclohexyl)-3-methylthiophene | O |
| W.201 | H | 5-fluoro-2-methyl-3',4'-dichlorobiphenyl | O |
| W.202 | H | 5-fluoro-2-methyl-3'-fluoro-4'-chlorobiphenyl | O |
| W.203 | H | 5-fluoro-2-methyl-3'-chloro-4'-fluorobiphenyl | O |
| W.204 | H | 5-fluoro-2-methyl-3',4'-difluorobiphenyl | O |
| W.205 | H | 2'-methyl-3-fluoro-4-[(methoxyimino)methyl]biphenyl | O |

TABLE W-continued
| Compound No. | R4 | A | X |
|---|---|---|---|
| W.206 | H | 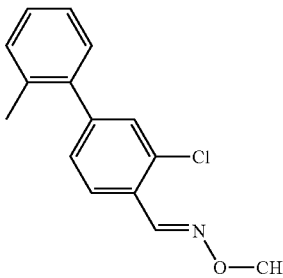 | O |
| W.207 | H | 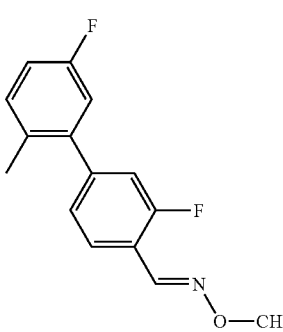 | O |
| W.208 | H | 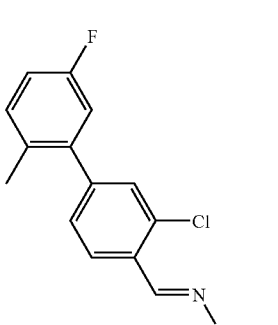 | O |
| W.209 | H | 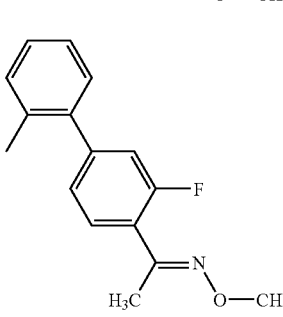 | O |
| W.210 | H | 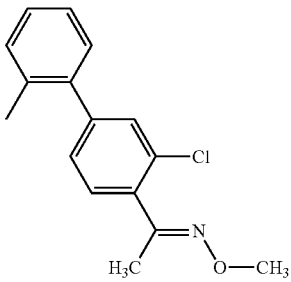 | O |
| W.211 | H | 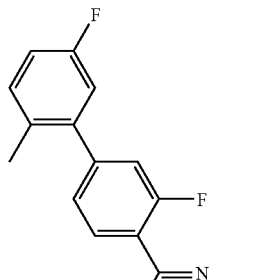 | O |
| W.212 | H | 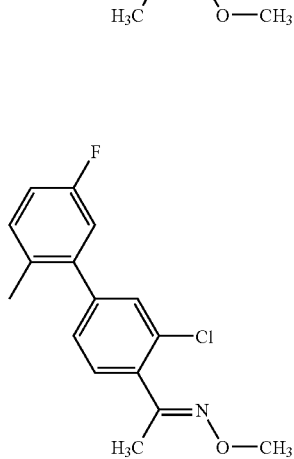 | O |
| W.213 | H | 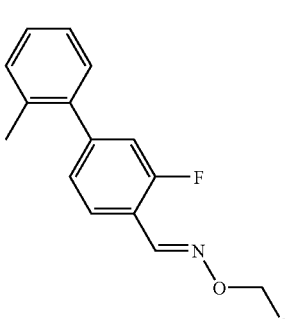 | O |
| W.214 | H | 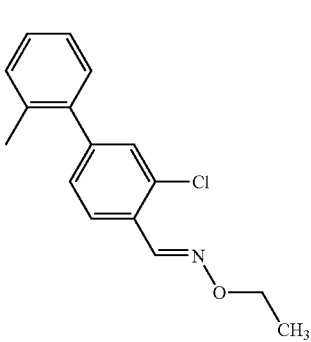 | O |

TABLE W-continued
| Compound No. | R₄ | A | X |
|---|---|---|---|
| W.215 | H | 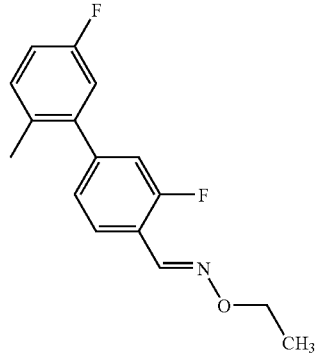 | O |
| W.216 | H | | O |
| W.217 | H | | O |
| W.218 | H | | O |
| W.219 | H | 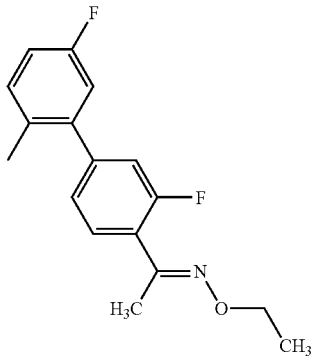 | O |
| W.220 | H | | O |
Table 1 provides 200 compounds of formula (I.a):
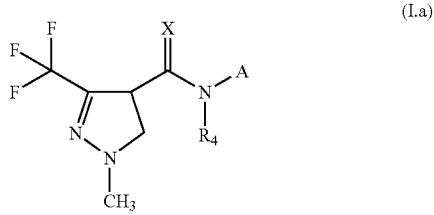
(I.a)
wherein R₄, A and X are as defined in Table 1.
Table 2 provides 200 compounds of formula (I.b):
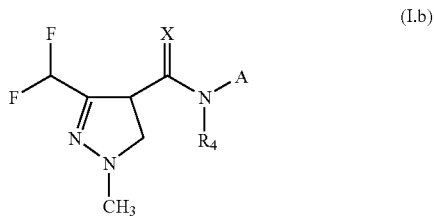
(I.b)
wherein R₄, A and X are as defined in Table 2.

Table 3 provides 200 compounds of formula (I.c)

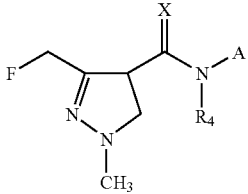

wherein $R_4$, A and X are as defined in Table 3.

Table 4 provides 200 compounds of formula (I.d):

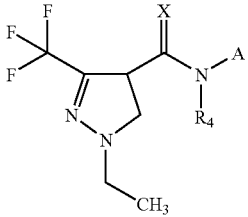

wherein $R_4$, A and X are as defined in Table 4.

Table 5 provides 200 compounds of formula (I.e):

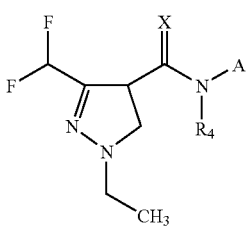

wherein $R_4$, A and X are as defined in Table 5.

Table 6 provides 200 compounds of formula (I.f):

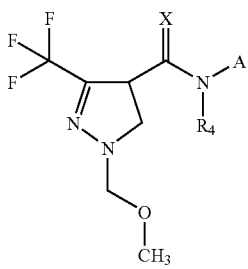

wherein $R_4$, A and X are as defined in Table 6.

Table 7 provides 200 compounds of formula (I.g):

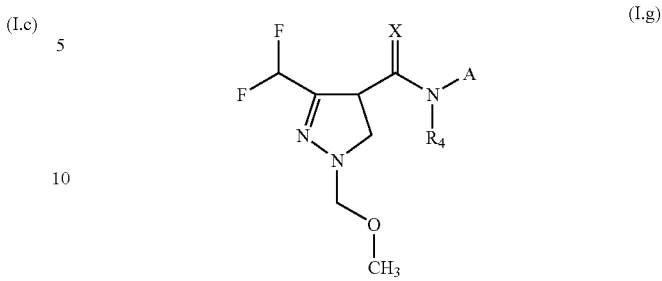

wherein $R_4$, A and X are as defined in Table 7.

Physical Data (Melting Points in ° C.):

Throughout this description, temperatures are given in degrees Celsius; "NMR" means nuclear magnetic resonance spectrum; MS stands for mass spectrum; and "%" is percent by weight, unless corresponding concentrations are indicated in other units.

The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

Table 8 shows selected melting point and selected NMR data, all with $CDCl_3$ as the solvent (unless otherwise stated, no attempt is made to list all characterising data in all cases) for compounds of Tables 1 to 7. Unless otherwise stated, the data relate to a cis/trans mixture of each compound.

TABLE 8

| Compound Number | $^1$H-NMR data (ppm/multiplicity/number of Hs) | m.p. (° C.) |
|---|---|---|
| 1.002 | | 176-178 |
| 1.006 | | 166-168 |
| 1.010 | | 183-184 |
| 1.097 | 0.82 (dd, 6H), 1.13 (d, 3H), 1.34-1.53 (m, 3H), 2.78 (q, 1H), 2.97 (s, 3H), 3.52 (q, 1H), 3.86-3.97 (m, 2H), 7.12-7.63 (m, 4H). | |
| 1.102 | 0.62-0.71 (m, 6H), 1.01 (d, 3H), 1.08-1.23 (m, 5H), 2.71 (q, 1H), 2.88 (s, 3H), 3.45 (q, 1H), 3.73-3.85 (m, 2H), 6.98-7.51 (m, 4H). | |
| 1.113 | | 135-140 |
| 1.117 | 0.10-0.22 (m, 4H), 0.41 (dq, 1H), 0.58 (q, 1H), 1.06 (d, 3H), 1.19-1.32 (m, 2H), 2.89 (s, 3H), 3.48 (q, 1H), 3.72-3.89 (m, 2H), 6.86-7.93 (m, 4H). | |
| 1.124 | 1.17 (d, 3H), 1.54-2.09 (m, 9H), 3.05 (q, 1H), 3.26 (s, 3H), 3.77 (q, 1H), 4.12-4.23 (m, 2H), 7.37-7.92 (m, 4H). | |
| 1.128 | | 187-188 |
| 1.133 | | 173-174 |
| 1.134 | | 127-157 |
| 1.145 | | 160-161 |
| 1.170 | 2.74 (s, 3H), 3.33 (t, 1H), 3.58 (t, 1H), 4.19-4.50 (m, 5H), 6.68-6.74 (m, 1H), 6.80-6.88 (m, 1H), 6.95-7.02 (m, 1H), 7.14-7.18 (m, 1H), 7.47 (s, 2H), 9.69 (bs, 1H). | |
| 1.171 | 2.43 (s, 3H), 2.60 (s, 3H), 2.90-3.21 (m, 3H), 3.38-3.45 (m, 1H), 3.60-3.75 (m, 2H), 7.20-7.60 (m, 12H), 8.06-8.35 (m, 4H), 8.87-8.93 (m, 2H). | |

TABLE 8-continued

| Compound Number | ¹H-NMR data (ppm/multiplicity/number of Hs) | m.p. (° C.) |
|---|---|---|
| 1.173 | | 123-125 |
| 1.177 | | 177-178 |
| 1.188 | 0.72 (dd, 6H), 1.10 (d, 3H), 1.27-1.43 (m, 3H), 2.81 (q, 1H), 2.89 (s, 3H), 3.42 (q, 1H), 3.73-3.85 (m, 2H), 6.92 (d, 1H), 7.15 (d, 1H). | |
| 2.006 | 2.87 (s, 3H), 3.46 (q, 1H), 3.61-3.69 (m, 2H), 5.72 (dt, 1H), 6.46 (br s, 1H), 7.10-8.08 (m, 8H). | |

FORMULATION EXAMPLES FOR COMPOUNDS OF FORMULA I

Example F-1.1 to F-1.3

Emulsifiable Concentrates

| Components | F-1.1 | F-1.2 | F-1.3 |
|---|---|---|---|
| compound of Tables 1 to 6 | 25% | 40% | 50% |
| calcium dodecylbenzenesulfonate | 5% | 8% | 6% |
| castor oil polyethylene glycol ether (36 mol ethylenoxy units) | 5% | — | — |
| tributylphenolpolyethylene glycol ether (30 mol ethylenoxy units) | — | 12% | 4% |
| cyclohexanone | — | 15% | 20% |
| xylene mixture | 65% | 25% | 20% |

Emulsions of any desired concentration can be prepared by diluting such concentrates with water.

Example F-2

Emulsifiable Concentrate

| Components | F-2 |
|---|---|
| compound of Tables 1 to 6 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 6 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 6 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 6 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 6 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 6 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action Against *Puccinia recondita*/wheat (Brown Rust on Wheat)

1 week old wheat plants cv. Arina are treated with the formulated test compound (0.02% active ingredient) in a spray chamber. One day after application, the wheat plants are inoculated by spraying a spore suspension ($1 \times 10^5$ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation.

Infestation is prevented virtually completely (0-5% infestation) with each of compounds 1.006, 1.010, 1.097, 1.117, 1.124, 1.128, 1.133, 1.177 and 1.188.

Example B-2

Action Against *Podosphaera leucotricha*/apple (Powdery Mildew on Apple)

5 week old apple seedlings cv. McIntosh are treated with the formulated test compound (0.02% active ingredient) in a spray chamber. One day after, the application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Infestation is prevented virtually completely (0-5% infestation) with each of compounds 1.002, 1.006, 1.010, 1.097, 1.124, 1.134 and 1.145.

Example B-3

Action Against *Venturia inaegualis*/apple (Scab on Apple)

4 week old apple seedlings cv. McIntosh are treated with the formulated test compound (0.02% active ingredient) in a spray chamber. One day after application, the apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Infestation is prevented virtually completely (0-5% infestation) with each of compounds 1.002, 1.006, 1.097, 1.117 and 1.145.

Example B-4

Action Against *Erysiphe graminis*/barley (Powdery Mildew on Barley)

1 week old barley plants cv. Regina are treated with the formulated test compound (0.02% active ingredient) in a spray chamber. One day after application, the barley plants are inoculated by shaking powdery mildew infected plants above the test plants. After an incubation period of 6 days at 20° C./18° C. (day/night) and 60% r.h. in a greenhouse the disease incidence is assessed.

Infestation is prevented virtually completely (0-5% infestation) with each of compounds 1.002, 1.010, 1.097, 1.117, 1.124, 1.134 and 1.188.

Example B-5

Action Against *Botrytis cinerea*/grape (Botrytis on Grapes)

5 week old grape seedlings cv. Gutedel are treated with the formulated test compound (0.02% active ingredient) in a spray chamber. Two days after application, the grape plants are inoculated by spraying a spore suspension ($1 \times 10^6$ conidia/ml) on the test plants. After an incubation period of 4 days at 21° C. and 95% r.h. in a greenhouse the disease incidence is assessed.

Infestation is prevented virtually completely (0-5% infestation) with compounds 1.006 and 1.145.

Example B-6

Action Against *Botrytis cinerea*/tomato (Botrytis on Tomatoes)

4 week old tomato plants cv. Roter Gnom are treated with the formulated test compound (0.02% active ingredient) in a spray chamber. Two days after application, the tomato plants are inoculated by spraying a spore suspension ($1 \times 10^5$ conidia/ml) on the test plants. After an incubation period of 4 days at 20° C. and 95% r.h. in a growth chamber the disease incidence is assessed.

Infestation is prevented virtually completely (0-5% infestation) with each of compounds 1.002, 1.010, 1.124, 1.133, 1.145, 1.173, 1.177 and 1.188.

Example B-7

Action Against *Septoria nodorum*/wheat (Septoria Leaf Spot on Wheat)

1 week old wheat plants cv. Arina are treated with the formulated test compound (0.02% active ingredient) in a spray chamber. One day after application, the wheat plants are inoculated by spraying a spore suspension ($5 \times 10^5$ conidia/ml) on the test plants. After an incubation period of 1 day at 20° C. and 95% r.h. the plants are kept for 10 days at 20° C. and 60% r.h. in a greenhouse. The disease incidence is assessed 11 days after inoculation. Infestation is prevented virtually completely (0-5% infestation) with compound 1.006.

Example B-8

Action Against *Helminthosporium teres*/barley (Net Blotch on Barley)

1 week old barley plants cv. Regina are treated with the formulated test compound (0.02% active ingredient) in a spray chamber. Two days after application, the barley plants are inoculated by spraying a spore suspension ($3 \times 10^4$ conidia/ml) on the test plants. After an incubation period of 4 days at 20° C. and 95% r.h. in a greenhouse the disease incidence is assessed.

Infestation is prevented virtually completely (0-5% infestation) with each of compounds 1.002, 1.006, 1.010, 1.097, 1.117, 1.124, 1.133, 1.134, 1.145, 1.173, 1.177 and 1.188.

Example B-9

Action Against *Alternaria solani*/tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed.

Infestation is prevented virtually completely (0-5% infestation) with each of compounds 1.006, 1.145 and 2.006.

Example B-10

Action Against *Uncinula necator*/grape (Powdery Mildew on Grapes)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed.

Infestation is prevented virtually completely (0-5% infestation) with each of compounds 1.002, 1.006, 1.097, 1.117, 1.124, 1.134 and 1.145.

Example B-11

Action Against *Sertoria tritici*/wheat (Septoria Leaf Spot on Wheat)

2 week old wheat plants cv. Riband are treated with the formulated test compound (0.2% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation.

Compounds 1.006 and 1.145 shows good activity in this test (<20% disease incidence).

What is claimed is:
1. A compound of the formula I:

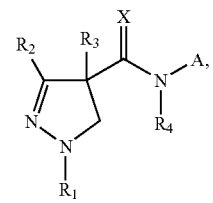

wherein:
$R_1$ is $C_{1-4}$ alkyl, $C_{1-4}$ haloalkyl, $C_{1-4}$ alkoxy($C_{1-4}$)alkyl or $C_{1-4}$ haloalkoxy($C_{1-4}$)alkyl;
$R_2$ is $C_{1-4}$ haloalkyl, $C_{1-4}$ alkyl, $C_{1-4}$ alkoxy($C_{1-4}$)alkyl, $C_{1-4}$ haloalkoxy or $C_{1-4}$ haloalkoxy($C_{1-4}$)alkyl;
$R_3$ is hydrogen, $C_{1-4}$ alkyl, $C_{2-4}$ alkenyl, $C_{2-4}$ alkynyl, halogen or cyano;
$R_4$ is hydrogen, $C_{1-4}$ alkyl, $CH_2CH=CHR_{4a}$, $CH_2C\equiv CR_{4b}$ or $COR_{4c}$;
$R_{4a}$ and $R_{4b}$ are each, independently, hydrogen, $C_1-C_6$alkyl, $C_1-C_6$haloalkyl, $C_2-C_6$alkenyl, $C_2-C_6$alkynyl, $C_3-C_7$cycloalkyl, $COOC_1-C_4$alkyl, $COOC_3-C_6$alkenyl, $COOC_3-C_6$alkynyl or CN;
$R_{4c}$ is $C_1-C_6$alkyl, $C_1-C_6$alkyl substituted by halogen, $C_1-C_6$alkoxy, $C_1-C_6$haloalkoxy, $C_1-C_6$alkylthio, $C_1-C_6$haloalkylthio, $C_1-C_6$alkoxy, $C_1-C_6$haloalkoxy, $C_3-C_6$alkenyloxy, $C_3-C_6$haloalkenyloxy, $C_3-C_6$alkynyloxy or $C_3-C_6$haloalkynyloxy;
X is oxygen or sulfur; and
A is

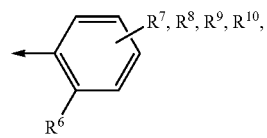

wherein:
$R^6$ is a $C_{1-12}$ alkyl, $C_{2-12}$ alkenyl or $C_{2-12}$ alkynyl group, which may be substituted by 1 to 6 substituents, each substituent independently selected from halogen, cyano, $C_{1-4}$ alkoxy, $C_{1-4}$ thioalkyl, $COO-C_{1-4}$ alkyl, $=N-OH$, $=N-O-(C_{1-4}$ alkyl), $C_{3-8}$ cycloalkyl, which may itself be substituted by 1 to 3 substituents, each substituent independently selected from $C_{1-4}$ alkyl, halogen, $C_{1-4}$ alkoxy and $C_{1-4}$ haloalkoxy, and $C_{4-8}$ cycloalkenyl, which may itself be substituted by 1 to 3 substituents, each substituent independently selected from $C_{1-4}$ alkyl, halogen, $C_{1-4}$ alkoxy and $C_{1-4}$ haloalkoxy;

or $R^6$ is a $C_{3-8}$ cycloalkyl, $C_{4-8}$ cycloalkenyl or $C_{5-8}$ cycloalkadienyl group, which may be substituted by 1 to 3 substituents, each substituent independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each substituent independently selected from $C_{1-4}$ alkyl, halogen, $C_{1-4}$ alkoxy and $C_{1-4}$ haloalkoxy, and phenyl, which may itself be substituted by 1 to 5 independently selected halogen atoms;

or $R^6$ is a $C_{6-12}$ bicycloalkyl, $C_{6-12}$ bicycloalkenyl or $C_{6-12}$ bicycloalkadienyl group, which may be substituted by 1 to 3 substituents, each substituent independently selected from halogen, $C_{1-4}$ alkyl and $C_{1-4}$ haloalkyl;

Z is $C_{1-4}$ alkylene;

p is 0 or 1;

$R^{25}$ is hydrogen, halogen, $C_{1-4}$ alkyl, $C_{1-4}$ haloalkyl, $C_{1-4}$ alkoxy$(C_{1-4})$alkyl, $C_{1-4}$ haloalkoxy$(C_{1-4})$alkyl or $Si(C_{1-4}$ alkyl$)_3$;

$R^{26}$ and $R^{27}$ are each independently hydrogen, halogen, $C_{1-4}$ alkyl or $C_{1-4}$ haloalkyl;

$R^{28}$ is hydrogen, $C_{1-4}$ alkyl or $C_{1-4}$ haloalkyl;

$R^a$, $R^b$, $R^c$ and $R^d$ are each independently hydrogen or a $C_{1-4}$ alkyl group, which may substituted by 1 to 6 substituents, each substituent independently selected from halogen, hydroxy, cyano, carboxyl, methoxycarbonyl, ethoxycarbonyl, methoxy, ethoxy, methylsulfonyl, ethylsulfonyl, difluoromethoxy, trifluoromethoxy, trifluoromethylthio and trifluorothiomethoxy;

Cy is a carbocyclic or heterocyclic 3-7 membered ring, which may be saturated, unsaturated or aromatic and which may contain a silicon atom as a ring member, wherein $(CR^aR^b)_m$ and $(CR^cR^d)_n$ may be bound either to the same carbon or silicon atom of Cy or to different atoms separated by 1, 2 or 3 ring members, wherein the carbocyclic or heterocyclic 3-7 membered ring may be substituted by 1 to 6 substituents, each substituent independently selected from halogen, $C_{1-4}$ alkyl, $C_{2-4}$ alkenyl, $C_{1-4}$ haloalkyl, $C_{1-4}$ alkoxy and halo-$C_{1-4}$ alkoxy;

$Y_1$ is $Si(O_{p1}Z^1)(O_qZ^2)(O_sZ^3)$, and provided that Cy contains a silicon atom as a ring member, then $Y_1$ may also be hydrogen;

$Z^1$ and $Z^2$ are each independently methyl or ethyl;

$Z^3$ is a $C_{1-4}$ alkyl or a $C_{2-4}$ alkenyl group, which may be interrupted by one heteroatom selected from O, S and N, and wherein the $C_{1-4}$ alkyl or $C_{2-4}$ alkenyl group may be substituted by 1 to 3 independently selected halogen atoms;

m and n are each independently 0, 1, 2 or 3;

$p_1$,q and s are each independently 0 or 1;

$R^7$, $R^8$, $R^9$, and $R^{10}$ are each independently hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ thioalkyl or $C_{1-4}$ thiohaloalkyl;

$R^{18}$ is hydrogen, $C_{1-4}$ alkyl, formyl, $C_{1-4}$ alkoxy$(C_{1-4})$ alkyl, $C(=O)C_{1-4}$ alkyl, which may be substituted by halogen or $C_{1-4}$-alkoxy, or $C(=O)O-C_{1-6}$ alkyl, which may be substituted by halogen, $C_{1-4}$ alkoxy or CN;

$R^{19}$, $R^{20}$, $R^{21}$, $R^{22}$, $R^{23}$ and $R^{24}$ are each independently hydrogen, halogen, hydroxy, $C_{1-4}$ alkoxy, $C_{1-6}$ alkyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring which itself may be substituted by 1 to 3 methyl groups, $C_{1-6}$ alkenyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring which itself may be substituted by 1 to 3 methyl groups, or a 3-7 membered carbocyclic ring, which may contain 1 heteroatom selected from nitrogen and oxygen, and wherein the 3-7 membered carbocyclic ring may be substituted by 1 to 3 methyl groups;

or $R^{19}R^{20}$ together with a carbon atom to which it is attached form a carbonyl-group, a 3-5 membered carbocyclic ring, which may be substituted by 1 to 3 methyl groups, $C_{1-6}$ alkylidene, which may be substituted by 1 to 3 methyl groups, or $C_{3-6}$ cycloalkylidene, which may be substituted by 1 to 3 methyl groups;

$m_1$ is 0 or 1;

$n_1$ is 0 or 1;

or a tautomer, stereoisomer or enantiomer of these compounds.

2. A compound of formula I according to claim 1, wherein $R_2$ is $C_{1-4}$ haloalkyl, $C_{1-4}$ alkyl, $C_{1-4}$ alkoxy$(C_{1-4})$alkyl or $C_{1-4}$ haloalkoxy$(C_{1-4})$alkyl.

3. A compound of formula I according to claim 1, wherein $R^6$ is:

a group of the form

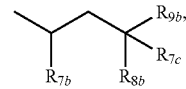

wherein:

$R_{7b}$ and $R_{7c}$ are each independently hydrogen, $C_1$-$C_3$alkyl or $C_1$-$C_3$haloalkyl; and $R_{8b}$ and $R_{9b}$ are each independently $C_1$-$C_3$alkyl or $C_1$-$C_3$haloalkyl;

or a group of the form

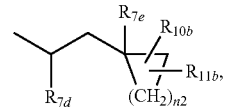

wherein:

$R_{7d}$ and $R_{7e}$ are each independently hydrogen, $C_1$-$C_3$alkyl or $C_1$-$C_3$haloalkyl;

$R_{10b}$ and $R_{11b}$ are each independently hydrogen or halogen; and $n_2$ is 1 or 2.

4. A compound according to claim 3, wherein $R_4$ is hydrogen.

5. A compound of formula I according to claim 1, wherein $R^6$ is a $C_{3-8}$ cycloalkyl group, which may be substituted by 1 to 3 substituents, each substituent independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each substituent independently selected from $C_{1-4}$ alkyl, halogen, $C_{1-4}$ alkoxy and $C_{1-4}$ haloalkoxy, and phenyl, which may itself be substituted by 1 to 5 independently selected halogen atoms.

6. A compound according to claim 5, wherein $R_4$ is hydrogen.

7. A method for protecting against phytopathogenic microorganisms, wherein a compound of formula I according to claim 1 or a composition comprising the compound of formula I as active ingredient is applied to the plants, to parts thereof or the locus thereof.

8. A composition for protecting against phytopathogenic microorganisms comprising the compound of formula I according to claim 1 and an inert carrier.

9. A compound of formula I according to claim 1, wherein:
$R_1$ is a methyl group;
$R_2$ is a difluoromethyl group;
$R_3$ is hydrogen; and
X is oxygen.

10. A composition for controlling and protecting against phytopathogenic microorganisms comprising the compound of formula I according to claim 9 and an inert carrier.

* * * * *